United States Patent [19]
Wrana et al.

[11] Patent Number: 6,017,755
[45] Date of Patent: Jan. 25, 2000

[54] MADR2 TUMOUR SUPPRESSOR GENE

[75] Inventors: Jeffrey Wrana; Liliana Attisano; Stephen W. Scherer, all of Toronto, Canada

[73] Assignee: HSC Research & Development Limited, Ontario, Canada

[21] Appl. No.: 08/701,582

[22] Filed: Aug. 22, 1996

[51] Int. Cl.[7] .............................. C12N 15/63; C12N 5/00; C07H 21/04
[52] U.S. Cl. ...................... 435/320.1; 435/325; 536/23.5
[58] Field of Search ................................ 435/320.1, 325; 514/44; 536/23.5

[56] References Cited

FOREIGN PATENT DOCUMENTS

WO 97/23697  6/1997  WIPO .
WO 97/39105  10/1997  WIPO .

OTHER PUBLICATIONS

Uchida et al. Somatic in vivo alterations of the JV18–1 gene at 18q21 in human lung cancers. Cancer Res. vol. 56:5583–5585, Dec. 15, 1996.

Frank et al. Evidence that loss of chromosome 18q is associated with tumor progression. Cancer Res. vol. 57:824–827, Mar. 1, 1997.

Weatherall Scope and limitations of gene therapy. British Med Bull. vol. 51(1):1–11, Jul. 1995.

Orkin et al. Report adn recommendations or the panel to assess the NIH investment in research on gene therapy, Dec. 5, 1995.

Lechleider et al. Serine phosphorylation, chromosomal localization, and transforming growth facto–beta signal transduction by human bsp–1. J. Biol. Chem. vol. 271(30):17617–17620, Jul. 26, 1996.

Riggins et al. Mad–related genes in the human. Nature Genet. vol. 13:347–349, Jul. 1996.

Sekelsky et al. Genetic characterization and cloning of Mothers Against dpp, a gene required fro decapentaplegic function in Drosophila melanogaster. Genetics vol. 139:1347–1358, Mar. 1995.

Baker et al. A novel mesoderm inducer, Madr2, functions in the activin signal transduction pathway. Genes and Dev. vol. 10:1880–1889, Aug. 15, 1996.

*Primary Examiner*—Nancy Degen
*Assistant Examiner*—William Sandals
*Attorney, Agent, or Firm*—Burns, Doane, Swecker & Mathis, L.L.P.

[57] ABSTRACT

A new human gene, MADR2, has been cloned and sequenced, and has been identified as a tumour suppressor gene. The protein encoded by the gene, MADR2, has been shown to participate in the TGFβ signalling pathway and to be phosphorylated on stimulation of the TGFβ receptor.

9 Claims, 10 Drawing Sheets

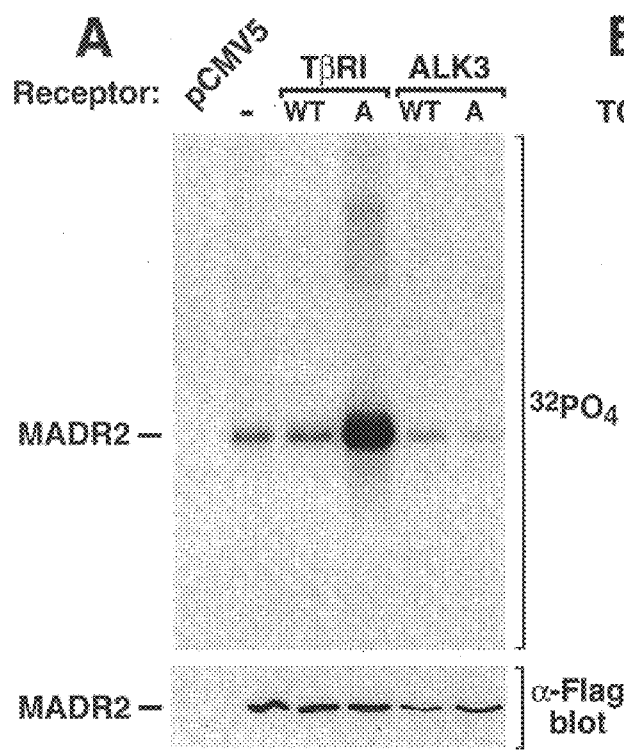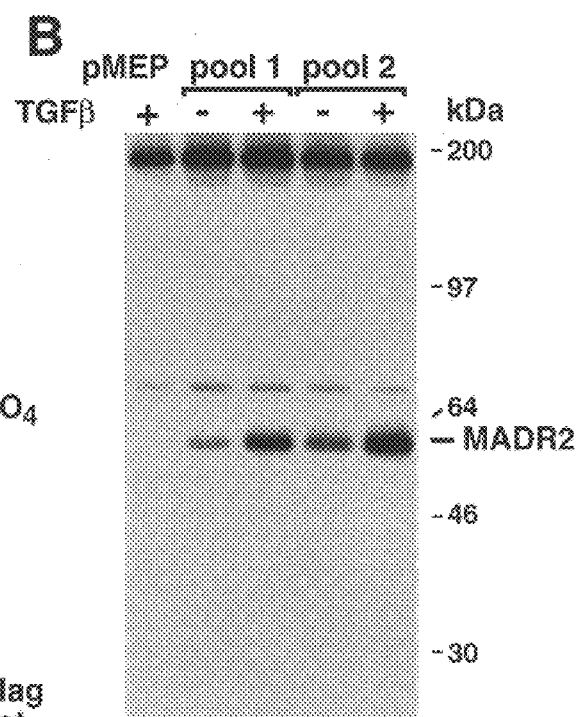
Figure 2A
Figure 2B

A
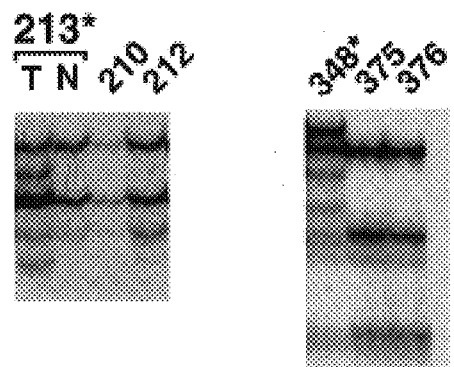
Figure 3A
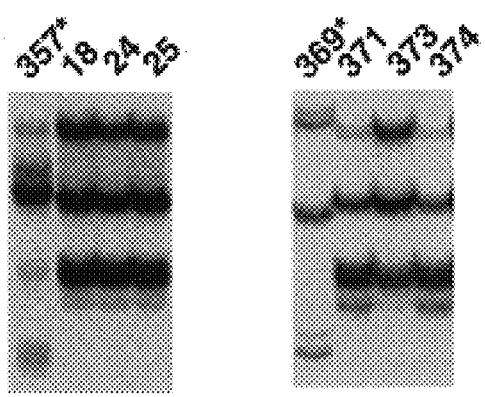
B
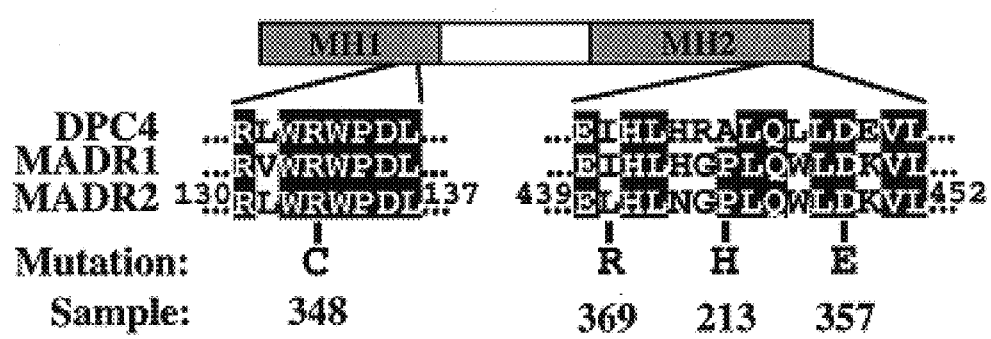
Figure 3B

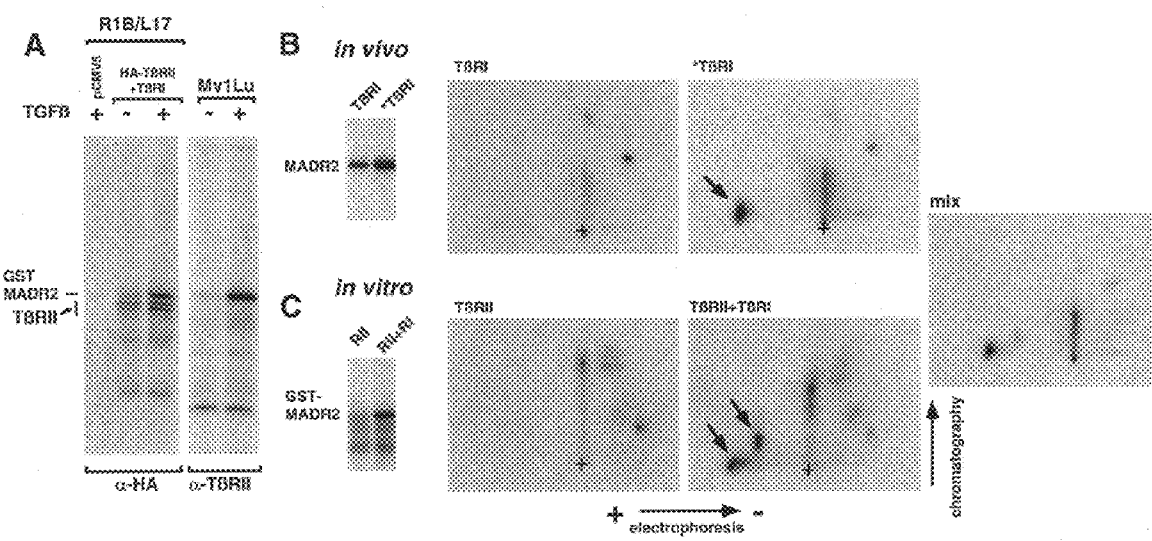

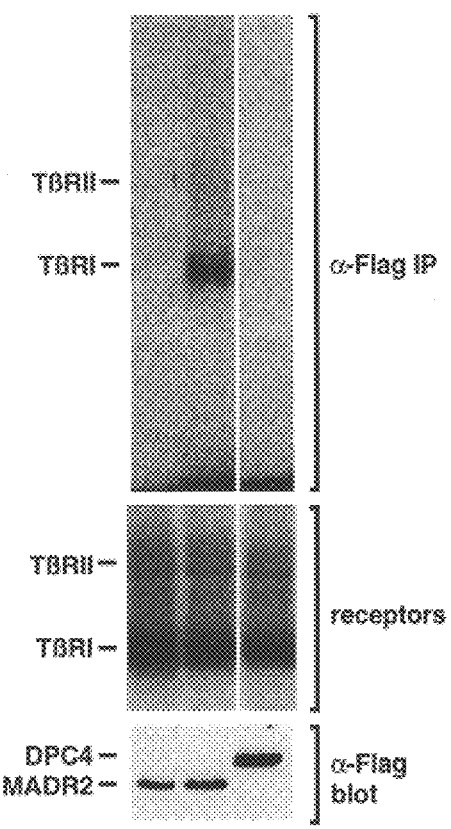
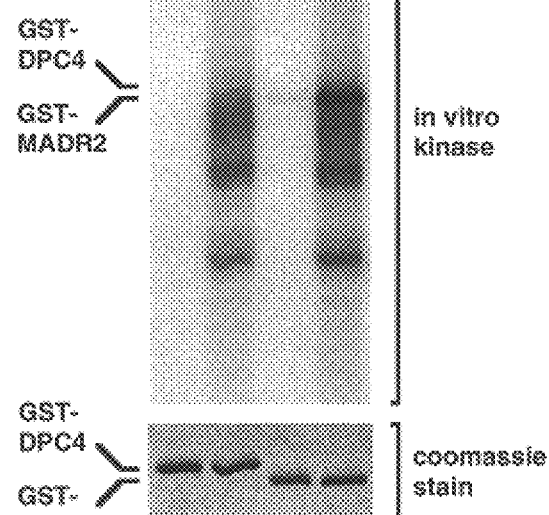
Figure 9A
Figure 9B

MADR2 TUMOUR SUPPRESSOR GENE

FIELD OF THE INVENTION

This invention relates to tumour suppressor genes and to use of such genes and their protein products in tumour screening and therapy. More particularly, this invention relates to the MADR2 gene, a member of the MAD-related gene family.

BACKGROUND OF THE INVENTION

Loss of sensitivity to negative growth regulators may be an important step in the development of malignant tumours. Transforming growth factor β, (TGFβ), a potent natural antiproliferative agent, is believed to play an important role in suppressing tumorigenicity. Comparisons of human colon carcinoma and melanoma cell lines have demonstrated a progressive loss of responsiveness to the growth inhibitory effects of TGFβ as tumour aggressiveness increases (Filmus et. al., 1993; Roberts et. al., 1993). Further, in certain tumour cells that have escaped TGFβ regulation, tumour aggressiveness has been directly correlated with an increased ability to secrete TGFβ, which may act in a paracrine manner to promote angiogenesis and inhibit the immune response (Roberts et al., 1993). Thus, an understanding of the molecular events associated with loss of TGFβ-responsiveness in tumours could provide major insights into the general mechanisms underlying the development of malignancies. At present, the mechanism for the escape from TGFβ regulation is not clear; mutational inactivation of components of TGFP signalling pathways could be one mechanism underlying acquisition of TGFβ resistance.

TGFβ signals through heteromeric receptor complexes of type I (TβRI) and type II (TβRII) serine/threonine (Ser/Thr) kinase receptors (Massagué et al., 1994; Miyazono et al., 1994). Receptor activation occurs on binding of ligand to TβRII which then recruits and phosphorylates TβRI which propagates the signal to downstream targets (Attisano et al., 1996; Chen et al., 1995; Wrana et al., 1994). Several studies have indicated that alterations in receptor expression or function may be involved in some cancers. For example, in a subset of colon cancer cell lines that display high rates of microsatellite instability, and in several TGFβ-resistant human gastric cancers, genetic changes in the type II receptor have been identified (Markowitz et al., 1995; Park et al., 1994). However, since the intracellular targets of the TGFβ receptors are poorly understood, the precise mechanism by which the disruption of TGFβ signalling pathways results in promoting tumorigenesis is unclear.

Recently, MADs (Mothers against dpp, decapentaplegic gene) and MADR (MAD-related proteins) have been identified in a variety of species as important components of the signal transduction pathway required for serine/threonine kinase receptor signalling (Graff et al., 1996; Goodless et al., 1996; Newfeld et al., 1996; Savage et al., 1996; Sekelsky et al., 1995; Thomsen, 1996). The Drosophila protein, MAD, and the closely related vertebrate protein MADR1, appear to be essential for signalling of the decapentaplegic (DPP) and bone morphogenetic protein 2 (BMP2) pathways, respectively, and MADR1 can specify BMP (bone morphogenetic proteins) specific biological responses (Graff, et al., 1996; Hoodless et al., 1996; Newfeld et al., 1996).

MADR1 is rapidly and specifically phosphorylated by the BMP2 pathway and not by the TGFβ-induced pathway (Hoodless et al., 1996). Furthermore, MADR1 redistributes from the cytoplasm to the nucleus upon introduction of signalling suggesting that MADs may have a nuclear function (Hoodless et al., 1996). Recently, a search for tumour suppressor genes implicated in pancreatic cancer led to the identification of the MAD-related gene, DPC4 (deleted in pancreatic carcinoma, Hahn et al., 1996a). However, the signalling pathway in which DPC4 functions is unknown.

A novel MAD-related gene, MADR2, has now been identified, sequenced and characterized as a candidate tumour suppressor gene. MADR2 protein has been shown to be regulated by TGFβ. Mutations of the MADR2 gene have been associated with colorectal carcinomas, strongly implicating the MADR2 protein in the development of human tumours. Knowledge of the function and localization of the mutated protein is useful in devising therapeutic strategies that are highly specific for neoplastic cells.

SUMMARY OF THE INVENTION

A new human gene, MADR2, has been identified and located on chromosome 18q21, a major tumour suppressor locus identified in a number of human cancers. The MADR2 gene encodes a protein of 467 amino acids. MADR2 is phosphorylated as a result of stimulation of the TGFβ receptor, but not as a result of stimulation of the Bone Morphogenetic Protein receptor. MADR2 is specifically regulated by TGFβ and functions downstream in the TGFβ signalling pathway.

MADR2 is mutated in approximately 6% of sporadic colorectal carcinomas. Mutational analysis of MADR2 in sporadic tumours has identified four missense mutations in colorectal carcinomas, including two losses of heterozygosity which represent the loss of one copy of a chromosomal region or a gene. Biochemical analysis demonstrates that three of these mutations lead either to a defect in expression of MADR2 or to a defect in TGFβ-mediated phosphorylation, indicating that these are inactivating mutations. These findings indicate that MADR2 is a tumour suppressor gene and that mutations acquired in colorectal carcinomas in this gene function to disrupt TGFβ signalling. Thus the MAD family of genes may represent a class of tumour suppressor genes implicated in the development of numerous human tumours.

Various aspects of the invention are summarized as follows. In accordance with a first aspect of the invention, an isolated nucleic acid is provided comprising a nucleotide sequence encoding MADR2 protein. The mammalian polynucleotide may be in the form of DNA, genomic DNA, cDNA, mRNA and various fragments and portions of the gene sequence encoding MADR2. The mammalian DNA is conserved in many species, including humans and rodents, for example mice. The mouse sequence encoding MADR2 shares a great deal of sequence identity with the human sequence encoding the same protein.

An isolated nucleic acid sequence for the MADR2 gene as cloned has been incorporated into a plasmid Bluescript.

According to one embodiment of the invention, a purified nucleotide sequence is provided comprising genomic DNA, cDNA, mRNA, anti-sense DNA or homologous DNA corresponding to the cDNA sequence of Sequence ID No.1.

In accordance with a further aspect of the invention, a substantially pure MADR2 protein is provided.

In accordance with a further aspect of the invention, a substantially pure polypeptide is provided comprising at least one functional domain of an MADR2 protein.

In accordance with a further aspect of the invention, a substantially pure polypeptide is provided comprising an antigenic determinant of an MADR2 protein.

In accordance with a further aspect of the invention, a method is provided for suppressing the neoplastic phenotype of a cell comprising administering to the cell an agent selected from the group consisting of (a) a nucleotide sequence encoding MADR2 protein;

(b) MADR2 protein, fragments, polypeptides and derivatives of polypeptides;

(c) a polynucleotide strand antisense to a mutant MADR2 gene;

(e) an agent to stabilize MADR2 protein; and (f) an agent to stimulate dephosphorylation of MADR2 protein.

In accordance with a further aspect of the invention, a diagnostic method is provided for determining if a subject carries a mutant MADR2 gene comprising the steps of (a) providing a biological sample from the subject; and (b) detecting in the sample a mutant MADR2 nucleic acid, a mutant MADR2 protein, or a mutant MADR2 activity.

In accordance with a further aspect of the invention, a method is provided for identifying allelic variants or heterospecific homologues of an MADR2 gene comprising (a) choosing a nucleic acid probe or primer capable of hybridizing to a human MADR2 gene sequence under stringent hybridization conditions;

(b) mixing said probe or primer with a sample of nucleic acids which may contain a nucleic acid corresponding to the variant or homologue;

(c) detecting hybridization of the probe or primer to the nucleic acid corresponding to the variant of homologue.

In accordance with a further aspect of the invention, a method is provided for producing antibodies which selectively bind to an MADR2 protein comprising the steps of administering an immunogenically effective amount of a MADR2 immunogen to an animal;

allowing the animal to produce antibodies tot he immunogen; and obtaining the antibodies from the animal or from a cell culture derived therefrom.

In accordance with a further aspect of the invention, a substantially pure antibody is provided which binds selectively to an antigenic determinant of an MADR2 protein selected from the group consisting of a normal MADR2 protein and mutant MADR2 protein.

In accordance with a further aspect of the invention, a method is provided for identifying compounds modulating expression of an MADR2 gene comprising contacting a cell with a test candidate wherein the cell includes a regulatory region of a MADR2 gene operably joined to a coding region; and detecting a change in expression of the coding region.

In accordance with a further aspect of the invention, a method is provided for treating a subjecting having a mutant MADR2 gene comprising administering to the subject a therapeutically effective amount of an agent selected from the group consisting of:

(a) an isolated nucleotide sequence encoding a normal MADR2 protein; and (b) a substantially pure normal MADR2 protein.

In accordance with a further aspect of the invention, a pharmaceutical composition is provided comprising an active ingredient selected from the group consisting of:

(a) an isolated nucleotide sequence encoding a normal MADR2 protein;

(b) a substantially pure normal MADR2 protein;

(c) an expression vector operably;

(d) a MADR2 antisense sequence; and (e) a substantially pure antibody which binds selectively to a mutant MADR2 protein and a pharmaceutically acceptable carrier.

In accordance with a further aspect of the invention, a method is provided of screening for an agent useful in treating a disorder characterized by an abnormality in a TGFβ signalling pathway, wherein the pathway involves an interaction between an MADR2 protein and an MADR2 binding partner, comprising screening potential agents for ability to disrupt or promote the interaction as an indication of a useful agent.

In accordance with a further aspect of the invention, a method is provided of preventing or treating a disorder in a mammal characterized by an abnormality in a TGFβ signalling pathway, wherein the pathway involves an interaction between a MADR2 protein and a MADR2 binding partner, comprising the step of disrupting or promoting said interaction in vivo.

SUMMARY OF THE DRAWINGS

The invention, as exemplified by preferred embodiments, is described herein with reference to the accompanying drawings in which:

FIG. 2A is an autoradiograph showing regulation of MADR2 phosphorylation by constitutively active type I receptors in COS-1 cells. COS-1 cells were transiently transfected with empty vector (pCMV5), Flag/MADR2 alone or Flag/MADR2 with the indicated wild type (WT) or constitutively active (ACT) type I-receptors and labelled with [$^{32}$P]phosphate. Flag/MADR2 was purified from cell lysates by immunoprecipitation using anti-Flag antibodies and analysed by SDS-PAGE and autoradiography. Total MADR2 protein, determined by immunoblotting, is shown in the bottom panel. The migration of MADR2 is indicated on the left.

FIG. 2B is an autoradiograph showing TGFβ-dependent phosphorylation in mink lung epithelial (Mv1Lu) cells. Mv1Lu cells transfected with Flag/MADR2 under the control of a metallothionein inducible promoter, were induced overnight with $Zn^{2+}$ and labelled with [$^{32}$P]phosphate in the absence (−) or presence (+) of TGFβ. MADR2 phosphorylation was analysed as in FIG. 2A. The migration of MADR2 is indicated on the right.

FIG. 3A shows non-denaturing gels illustrating single-strand conformation polymorphism (SSCP) analysis of MADR2. Mutation 348 is from region 1 and mutations 213, 357 and 369 are from region 3. Sample 213 is represented by T (tumour) and N (Normal colon tissue). In each case, the mutant is followed by samples with wild-type SSCP banding patterns that were run in adjacent lanes.

FIG. 3B shows a summary of predicted amino acid alterations resulting from MADR2 mutations. The amino acid sequence of MADR2, from amino acid 130 to 137 of the MH1 domain (Sequence ID No:19) and from amino acid 439 to 452 of the MH2 domain (Sequence ID No:20), are aligned with the corresponding regions in MADR1 (Sequence ID Nos:17 and 18 respectively) and DPC-4 (Sequence ID Nos:15 and 16 respectively). Conserved sequences are highlighted (Black box). The location of the missense mutations and the predicted amino acid changes are indicated.

FIG. 7A is an autoradiograph showing phosphorylation of MADR2 in vitro by isolated receptor complexes. Non-transfected Mv1Lu cells or L17 cells transiently transfected with empty vector (pCMV5) or both TβRI and HA-tagged TβRII were incubated with (+) or without (−) TGFβ. The receptor complexes were isolated by immunoprecipitation using α-HA or α-TβRII antibodies as indicated and then incubated in kinase assay buffer and bacterially expressed MADR2 fusion protein (GST-MADR2) as substrate.

FIG. 7B is a polyacrylamide gel showing in vivo phosphorylation of MADR2. COS-1 cells transfected with Flag-MADR2 and either wild type (TβRI) or constitutively active (*TβRI) were labelled and MADR2 was purified by immunoprecipitation and run on a gel. The right hand panels show two dimensional phosphopeptide mapping of tryptic gel digests of gel purified MADR2 that was phosphorylated in vivo.

FIG. 7C is an autoradiograph showing in vitro phosphorylation of MADR2. COS-1 cells were transfected with TβRII and TβRI, incubated with TGFβ, and the isolated receptors were subjected to an in vitro kinase assay as described for FIG. 7A. The right hand panels show phosphopeptide mapping of MADR2 phosphorylated in vitro. The arrows point to the specific phosphopeptides that are phosphorylated by the TGFβ receptor.

FIG. 9A is an autoradiograph showing the specificity of receptor association. COS-1 cells transfected with Flag-MADR2 or FlagDPC4 together with TβRII and either wild type (WT) or kinase deficient (KR) TβRI were affinity-labelled with [$^{125}I$]TGFβ. FlagMADR2 and FlagDPC4 were immunoprecipitated with anti-Flag M2 antibodies and associated receptors visualized by SDS-PAGE and autoradiography. To confirm constant receptor expression levels, aliquots of total cell lysates were similarly examined (receptors, middle panel). The bottom panel shows the equivalent expression of FlagMADR2 protein as determined by the immunoblotting of total cell lysates using anti-M2 antibody.

FIG. 9B is an autoradiograph showing the phosphorylation of MADR2 and DPC4 in vitro. COS-1 cells transiently transfected with empty vector (−) or with TbRI and HA-tagged TbRII were incubated with TGFb. Cells were lysed and receptor complexes isolated by immunoprecipitation using anti-HA antibodies. Receptor complexes were subjected to an in vitro kinase assay with bacterially expressed MADR2 or DPC4 as indicated (substrate). Phosphorylation of MADR2 and DPC4 was visualized by SDS-PAGE and autoradiography. The middle panel is a Coomassie stained gel indicating the relative level of MAD-related proteins.

DETAILED DESCRIPTION OF THE INVENTION

Figure 1:
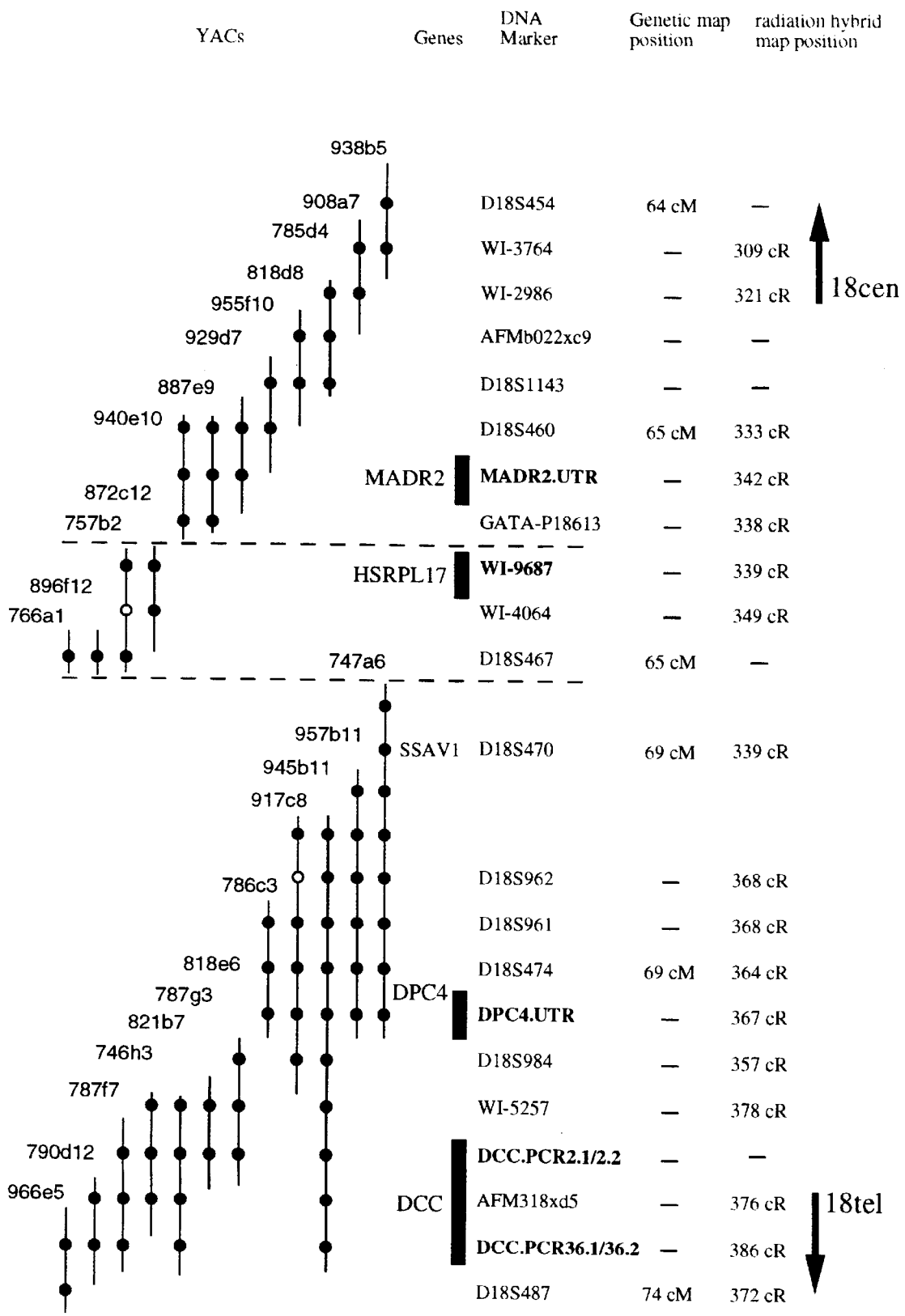
FIG. 1 shows the position of MADR2, DPC4, and DCC, within the context of the Whitehead Institute RH framework map (Hudson et al., 1996) and the Genethon genetic linkage map. MADR2, DPC4, and DCC were shown to map 9.32 cR, 10.31 cR, and 8.0 cR from D18S460, D18S984, and WI-5257, respectively. An STS contig map of a subset of YAC clones from the Whitehead Institute/MIT Center for Genome Research contig WC18.5 (Hudson et al., 1995) is also shown to more precisely order the 3 genes and surrounding markers. Black solid circles on the YACs indicate the DNA markers determined to be positive, while open circles represent markers that were expected to be positive but were not. The 2 vertical dashed lines delineate gaps in the YAC contig. YACs 766a1, 785d4, 786c3, 787f7, 787g3, 887e9, 896f12, 908a7, 938b5, 940e10, 955f10 are chimeric. DNA marker DCC.PCR2.1/2.2 and DCC.PCR36.1/36.2 represented the 5'- and 3'-end of DCC, respectively.

The present invention is concerned with the identification and sequencing of the mammalian MADR2 gene and the characterisation of the MADR2 protein. The gene has been identified, cDNA isolated and cloned, and its transcripts and gene products identified and sequenced.

The invention also relates to the identification of mutant forms of MADR2 and their association with colorectal cancer.

The invention enables screening methods for the diagnosis of colorectal cancer and other related malignancies and also enables therapeutic methods for the treatment of such malignancies.

With the identification of the gene sequence and the gene product, probes and antibodies raised to the gene product can be used in a variety of hybridization and immunological assays to screen for and detect the presence of either a normal or mutated gene or gene product.

Patient therapy through removal or blocking of the mutant gene product, as well as supplementation with the normal gene product by amplification, by genetic and recombinant techniques or by immunotherapy can now be achieved. Correction or modification of the defective gene product by protein treatment immunotherapy (using antibodies to the defective protein) or knock-out of the mutated gene together with wild-type supplementation is now also possible. Malignancies could also be controlled by gene therapy in which the gene defect is corrected in situ or by the use of recombinant or other vehicles to deliver a DNA sequence capable of expressing the normal gene product, or to deliver a deliberately mutated version of the gene product whose effect counterbalances the deleterious consequences of the mutated gene product on the affected cells of the patient. The present invention also allows for the development of novel drugs to mimic the effect of the normal protein or for drugs used as antagonists of the protein.

Identification of Human MADR2 Gene

MAD and MAD-related proteins identified in Drosophila (MAD), *C. elegans* (sma-2, sma-3, sma-4), Xenopus (Xmad1 and Xmad2) and humans (MADR1, DPC4) have been demonstrated to play a crucial role in signal transduction by members of the TGFβ superfamily (Graff et al., 1996; Hahn et al., 1996a; Hoodless et al., 1996; Savage et al., 1996; Sekelsky et al., 1995; Thomsen 1996). The MAD-related molecule which may function specifically in the TGFβ pathway was cloned by searching a database of expressed sequence tags which are randomly spaced, unique sequences of cDNA (Lennon et al., 1996). Two non-overlapping partial clones were identified which contained open reading frames that displayed similarity either to the amino or the carboxy terminus of MADR1. To obtain the full-length coding sequence, primers encoding the predicted start and stop codons were designed for polymerase chain reaction and a human kidney cDNA library was used as a template. A contiguous sequence of 1605 base pairs was obtained (Table 1) which includes an open reading frame of 467 amino acids (Table 2). The predicted protein is related to MAD and MADR1and thus this protein was named MADR2.

The cDNA sequence of MADR2 (Sequence ID No:1) is shown in Table 1 which contains 5' and 3' UTR and encoding the entire open reading frame of MADR2. The coding region spans 1401 nucleotides resulting in a predicted gene product of 467 amino acids (Sequence ID No: 2). The total length of the MADR2 cDNA spans 1605 nucleotides with a 36 nucleotide 5' UTR and a 168 nucleotide 3' UTR. The complete cDNA sequence allows one skilled in the art to develop probes and primers for the identification of homologous sequences, ie. sequences sharing sequence identity, and for the identification of mutations within the cDNA. Both 5' and 3' regions may also prove useful for encoding binding sites for agents which may up- or down-regulate the gene, further delineating the MADR2 pathway and function. The cDNA sequence is also useful for protein expression in appropriate vectors and hosts to produce MADR2 protein. The DNA sequence of the MADR2 gene as cloned has been incorporated into a Bluescript plasmid, deposited with the ATCC, Rockville, Md., under ATCC Accession No. 97691 on Aug. 22, 1996, where the deposit was made under the terms of the Budapest Treaty.

The characteristics and function of the cloned MADR2 cDNA sequence may be analyzed by introducing the sequence into various cell types. The function of the MADR2 may then be examined under different physiological conditions. The MADR2 sequence may be manipulated to understand the expression of the gene and gene product. Alternatively, cell lines may be produced which overexpress the gene product allowing purification of MADR2 for biochemical characterization, large-scale production, antibody production and patient therapy.

Human MADR2 Protein

The human MADR2 protein is encoded by an open reading frame of 467 amino acids coded by a contiguous sequence of 1401 base pairs. This protein has an approximate molecular weight of approximately 60 kDa. An alignment of the predicted amino acid sequences of human MADR1, MADR2 and DPC4 (Table 4) indicates that MADR2 is more closely related to MADR1than to DPC4, a candidate tumour suppressor gene in pancreatic cancer (Hahn et al., 1996a). The highest degree of sequence conservation between MADR2 and other MADs lies in the MH1 (MAD homology 1) and MH2 (MAD homology 2) domains which are located in the amino and carboxy termini, respectively (Tables 3 and 4).

The central regions of these proteins are more divergent and are particularly rich in serine and threonine residues.

MADR2 has been demonstrated to be expressed ubiquitously in human cells. This expression pattern and the high degree of amino acid sequence conservation across species indicate the likely importance of MADR2 in cellular regulation.

Identification of a Mouse MADR2 Gene

A murine homologue for the MADR2 gene, mMADR2, was recovered by screening a mouse cDNA library with a labeled human DNA probe which recovered the full length transcript. Sequencing of the consensus cDNA transcript of the murine homologue revealed substantial amino acid identity with the human MADR2 protein. The mouse MADR2 cDNA sequence is identified as Sequence ID No: 3 and the deduced amino acid sequence is identified as Sequence ID No: 4. The MADR2 gene is highly conserved in the mouse compared with the human, indicating that this mouse gene is orthologous to the human gene. This high level of conservation makes it possible to clone MADR2 from mouse and other species genomic libraries using human MADR2 probes and to identify and characterize the MADR2 gene in other species. The isolation of the mMADR2 gene will also allow for characterization of the physiological significance of the wild-type and any mutated MADR2 gene and gene products in a transgenic mouse model.

Mouse MADR2 Protein (mMADR2)

The mouse MADR2 protein, SEQ ID No. 4, has 467 amino acids encoded by an open reading frame of 1401 nucleotides. The protein has an approximate molecular weight of approximately 60 kDa. Alignment of the predicted mouse and human MADR2 amino acid sequences indicates a high degree of sequence conservation. This homologous sequence identity is extended to the MH1 and MH2 regions of the protein, which suggests that these regions are important for the functioning of the protein.

Phosphorylation of MADR2 by TGFβ Signalling Pathways

To examine which serine/threonine kinase receptor-activated pathways regulate MADR2, constitutively active type I serine/threonine kinase receptors were employed. These type I receptors, generated by the introduction of a charged residue in the highly conserved GS domain (Attisano et al., 1996; Hoodless et al., 1996; Wieser et al., 1995), signal in the absence of ligand and type II receptors (Wieser et al., 1995). To facilitate this analysis, a mammalian expression vector which encodes a Flag epitope tag at the amino terminus of MADR2 Flag/MADR2) was constructed. In order to determine whether MADR2 is a target of TGFβ or BMP signaling pathways, COS cells were transiently transfected with FlagMADR2 alone or together with wild type or activated TβRI or ALK-3 (a BMP type I receptor). The FlagMADR2 was immunoprecipitated from [$^{32}$P]phosphate-labeled transfectants using an anti-Flag monoclonal antibody.

Analysis of the immunoprecipitates revealed that phosphorylation of MADR2 was unaffected by the coexpression of wild type TβRI, wild type ALK-3 or activated ALK-3 (FIG. 2). In contrast, MADR2 phosphorylation was substantially increased in cells cotransfected with activated TβRI. In contrast, MADR1 was phosphorylated only in cells cotransfected with constitutively active ALK-3 (data not shown).

It was also found that MADR2 phosphorylation was regulated in a TGFβ-dependent manner. This was established using Mv1Lu mink lung epithelial cell lines stably transfected with Flag MADR2 under the control of an inducible metallothionein promoter (Wrana et al., 1992). The Mv1Lu epithelial cells express both type I and type II receptors and are TGFβ sensitive. Two independent pools of cells expressing FlagMADR2 in a zinc-inducible manner were generated and the regulation of MADR2 phosphorylation in response to TGFβ was examined. Analysis of MADR2 immunoprecipitated from [$^{32}$P]phosphate-labeled cells that were untreated or treated with TGFβ revealed a ligand-dependent phosphorylation in both pools (FIG. 2B). Thus, brief treatment of epithelial cells with TGFβ induced the phosphorylation of MADR2.

These results demonstrated that at least in the case of MADR1 and MADR2, these molecules lie in specific serine/threonine kinase receptor signalling pathways. Studies in Xenopus further highlight this specificity, since overexpression of specific MADs can recapitulate the biological response normally induced by activation of the upstream receptors. These data indicate that MADR2 is regulated by TGFβ and not BMP receptor signaling pathways and along with the known function of MAD proteins in serine/threonine kinase receptor signal transduction, suggest that MADR2 plays a role in mediating TGFβ signals.

Localization of MADR2 to chromosome 18q21

The chromosomal localization of MADR2 was determined using a combination of radiation hybrid (RH) mapping, yeast artificial chromosome (YAC) contig analysis, and fluorescence in situ hybridization (FISH). In the FISH approach, cloned DNA is labeled in vitro using nucleoside triphosphates that contain a fluorescent nucleoside derivative. The labeled DNA is then visualized by fluorescence of regions where the labeled DNA probe hybridizes with the chromosomal segments. Alternatively, the cloned DNA can be labeled in vitro using nucleoside triphosphates conjugated to biotin which is a naturally occurring prosthetic group that can be used as a molecular tag.

PCR primers designed from the 3'-UTR of MADR2 were initially used to screen the GeneBridge 4 RH panel (Walter et al., 1994) and the results indicated that the gene resides on chromosome 18q21 approximately 9.3 cR from D18S460. The same primers were also used to screen the CEPH megaYAC library (Chumakov et al., 1995) and 5 YACs (739a3, 749d11, 887e9, 929d7, 940e10) were identified. These clones were shown previously by the Whitehead Institute/MIT Center for Genome Research to map within a well-defined YAC contig on chromosome 18 (named WC18.5). This contig encompassed the same DNA marker, D18S460, that was linked to MADR2 on the RH map (Hudson et al., 1995) and further analysis of the YACs identified 3 clones that contained both MADR2 and D18S460 (FIG. 1). The cytogenetic position of MADR2 was confirmed further by FISH mapping two gene-specific P1-derived artificial chromosome clones (PACs 66i18 and 201n19) to 18q21.

The fact that MADR2 mapped to chromosome 18q21 allowed for the determination of its relative location with respect to DPC4 and DCC, which also map to 18q21 (Hahn et al., 1996a) and have been shown to be frequently deleted in pancreatic cancer (Hahn et al., 1996a: Hahn et al., 1996b), respectively. Accordingly, gene-specific sequence-tagged sites (STSs) for DPC4 and DCC were tested against the RH panel and all of the YAC clones from the WC18.5 contig. The YAC clones containing the DNA were then ordered using PCR and screening for the sequence-tagged sites. In this method, contiguous overlapping YAC clones were ordered by subjecting aliquots of DNA prepared from each YAC clone to PCR amplification using primer pairs corresponding to the ends of various sequence-tagged sites (STSs). Only those clones containing STSs with ends complementary to particular primers are amplified. Electrophoretic analysis then shows which YAC clones contain which STSs. Based on the gel patterns, the YAC clones can be ordered. Using a published YAC and RH map (Hudson et al., 1995) as a framework, the following order was established: 18cen-MADR2-DPC4-DCC-18qter (FIG. 1). Both the YAC and RH data for the genes were in complete agreement. However, the precise physical distance separating the genes was difficult to establish since the map was based only on STS-content and because 2 gaps are present within the YAC contig. It was nevertheless evident that MADR2 mapped to the same cytogenetic band as DPC4 and DCC and within close enough physical proximity to suggest that it may also be frequently deleted in tumours demonstrating loss of heterozygosity (LOH) of 18q21.

DPC4, a MAD-related gene, has also been mapped to 18q21 in close proximity to MADR2 and has been identified as a candidate tumour suppressor in pancreatic carcinoma (Hahn et al., 1996a). A similar situation exists for APC (adenomatous polyposis coli) and MCC (mutated in colon cancer) on chromosome 5q21. APC mutations contribute to the development of sporadic and familial colorectal cancers, both APC and MCC are located in close physical proximity, share significant sequence identity with coiled-coil class protein and are frequently deleted concurrently in many different cancers. MADR2 may share a similar functional relationship with DPC4. DPC4 may function downstream of a different TGFβ superfamily member whose function is important in controlling the growth of pancreatic cells. However, it is also possible that DPC4 might also function in the TGFβ signaling pathway, as suggested recently for the multiple sma genes in BMP signaling in C. elegans (Savage et al., 1996). This raises the possibility that MADR2 and DPC4 together may function in a cooperative way and that mutations in either gene would allow cells to escape from TGFβ sensitivity. Thus, both MADR2 and DPC4 could be implicated as tumour suppressor genes in a variety of tumours of the gastrointestinal tract.

MADR2 is Mutated in Colorectal Carcinoma

A variety of human tumours were examined for mutations in MADR2 using single strand conformation polymorphism (SSCP) analysis of cDNA, focussing on the MH1 and MH2 domains of MADR2, which display the highest degree of similarity amongst members of the MAD family.

Initially screened were 101 auxiliary node-negative breast carcinomas and 76 sarcomas (including 35 osteosarcomas). These did not reveal any mutations, with the exception of a benign polymorphism (R415R) in one breast cancer sample. In a screen of 66 sporadic colon carcinomas, four missense mutations (6%)were identified. The missense mutations identified were as follows:

|    | Codon | Mutation   | Amino Acid Change   |
|----|-------|------------|---------------------|
| 1. | 445   | CCT to CAT | Pro to His (P445H)  |
| 2. | 440   | CTT to CGT | Leu to Arg (L440R)  |
| 3. | 450   | GAC to GAG | Asp to Glu (D450E)  |
| 4. | 133   | CGC to TGC | Arg to Cys (R133C)  |

Figure 4:
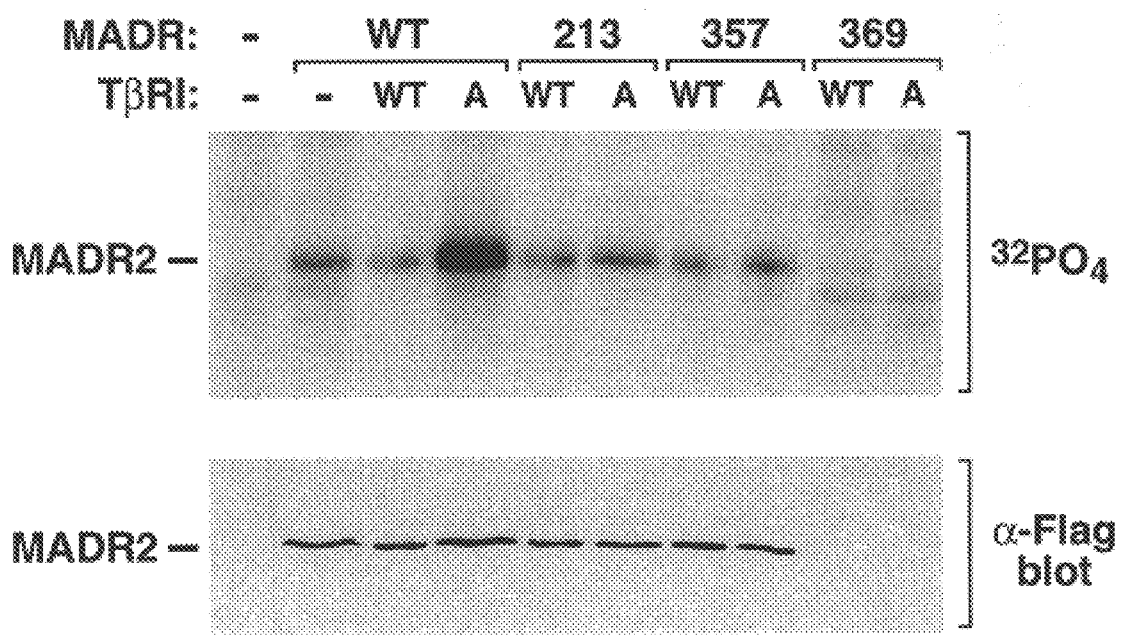
FIG. 4 shows a western blot of COS-1 cells transiently transfected with empty vector (−), Flag/MADR2 wild type (WT) alone, or FlagMADR2 wild type or mutated (212, 357 or 369) together with wild type (WT) or constitutively active (A) TβRI. Flag/MADR2 was purified from cell lysates and was analysed by SDS-PAGE and autoradiography. Total MADR2 protein is shown in the bottom panel. The migration of MADR2 is indicated on the left.

The first three of these altered highly conserved residues are within the MH2 domain and involved two nonconservative (P445H and L440R) and one conservative (D450E) change (FIG. 4 and Table 1). The fourth missense mutation mapped to the MH1 domain and resulted in the alteration of a highly conserved arginine residue to a cysteine residue (R133C; FIG. 3B and Table 3). In the three cases where normal tissue was available, MADR2 was found to have wild-type sequence, indicating that these mutations were acquired as somatic events. SSCP band intensities were also analyzed. Comparison of mutant and wild type alleles in each tumour sample showed that tumours 357 and 369 had little or no wild type message, suggesting loss of heterozygosity (LOH) at this locus. No germline mutations of MADR2 have been found in a panel of lymphoblastoid lines generated from 15 patients who had a strong family history of colorectal tumours or who presented with colorectal cancer at a young age.

Tumour suppressor genes are often inactivated when one allele acquires a somatic mutation and the second allele is lost, typically through deletion (Cavenee et al., 1983). LOH at 18q21 has been identified in numerous human cancers (Vogelstein et al., 1988; Yamaguchi et al., 1992). MADR2 mapping to this region of the human genome suggested the possibility that MADR2 acts as a tumour suppressor. A random screen of 76 sarcomas, 101 breast carcinomas and 66 sporadic colorectal carcinomas identified four mutations specific to colon carcinoma, of which at least three were acquired somatically. In two of these samples, wild type MADR2 could be clearly detected, which may be due to the presence of normal tissue in the specimen or to tumour heterogeneity. Nonetheless, in two of the cases there was a very low expression or loss of the normal allele suggestive of an LOH of MADR2. Together with the observation that these mutations are likely to be inactivating, these results provide strong evidence that MADR2 is a tumour suppressor gene in sporadic colorectal cancers.

Although only 4 missense mutations have been identified to date, it is anticipated that additional mutations will be found in colorectal malignant tissues and in other malignant tissues as well. Each of the mutations identified or a combination of these mutations may be responsible for the development of colorectal carcinoma. It is also possible that other types of mutations may also be found such as any form of nucleotide sequence substitution, insertion or deletion that leads to a changes in the predicted amino acid sequence or that leads to aberrant transcript processing, level or stability. It is also possible that while no polymorphisms have been found as yet in colorectal samples, it is possible that polymorphisms may still exist and be identified.

Mutated MADR2 and Regulation by TGFβ

Mutation of a conserved residue within the MH2 domain of MADR1 has been shown to disrupt regulation by the BMP2 signalling pathway and correlates with the loss of functional protein (Hoodless et al., 1996; Savage et al., 1996; Sekelsky et al., 1995). To determine the potential consequences of the missense mutations identified in the MH2 domain of MADR2, the regulation of the mutant proteins by the TGFβ signalling pathway was investigated. The mutations L440R, P445H and D450E were introduced into wild type Flag/MADR2 vectors and expressed in COS-1 cells together with either wild type or constitutively active TβRI. Relative phosphorylation levels were assessed by immunoprecipitation of MADR2 protein from [$^{32}$P] phosphate-labelled cells and quantifying protein levels by western-blotting of whole cell lysates. When wild type MADR2 was coexpressed with activated TβRI, typical elevations in phosphorylation of MADR2 were observed (FIG. 4). In contrast, two of the MADR2 mutants, 213 and 357 (P445H and D450E, respectively), showed no alterations in relative phosphorylation upon coexpression with activated receptors. Thus, both the nonconservative P445H and the conservative D450E mutations disrupted the regulation of MADR2 phosphorylation. No stable expression of the 369 mutant (L440R) in COS cells was detected (FIG. 4). This indicated that the L440R mutation disturbs the stability of the nascent protein or interferes with translation of the mRNA. These results provide strong evidence that the missense mutations in MADR2, identified in colorectal carcinomas, lead to disruption of protein function and concomitant loss of TGFβ sensitivity in the target cells.

Analyses of the regulation of MADR2 by TGFβ signalling pathways demonstrated that the somatic mutations characterized can lead to two distinct defects. Two of the mutations in the MH2 domain characterized from tumours disrupted the regulation of MADR2 phosphorylation by TGFβ signalling pathways. Studies on MADR1 have previously identified a mutation within the MH2 domain that blocks phosphorylation by the BMP signalling pathways (Hoodless et al., 1996). This particular mutation generates null phenotypes in Drosophila or C. elegans providing evidence that these types of mutations yield non-functional protein products (Savage et al., 1996; Sekelsky et al., 1995). The analysis of the nonconservative L440R mutation revealed that this change results in a defect in stable expression of MADR2 protein. This may be due to a defect in translation or stability of the protein product and likely results in loss of MADR2 expression in target cells. Regardless of the mechanism, the mutations identified in colorectal carcinoma are most likely inactivating leading to a loss of functional protein in the tumours.

MADR2 Mutants are Biologically Inactive in Xenopus Mesoderm Induction Assays

Xenopus blastula stage ectoderm can differentiate into mesodermal tissues in response to particular members of the TGFβ superfamily (reviewed in Kessler and Melton 1994, Wall et al., 1994). For example, BMPs induce ventral mesoderm such as blood whereas activin induces dorsal types of mesoderm such as muscle and notochord. Similar to the common biological responses observed for activin and TGFβ in mammalian cells (Carcamo et al., 1994), TGFβ can also induce dorsal mesoderm in caps ectopically expressing TβRII receptor (Bhushan et al., 1994). Further, overexpression of a Xenopus homolog of TβRI that is 98% identical to TβRI in the kinase domain similarily results in formation of dorsal mesoderm (Mahony et al., 1995). Overexpression of the Xenopus Mad-related proteins Xmad1 and Xmad2 in the ectoderm mimics these effects. Thus, Xmad1 induces ventral mesoderm while Xmad2, like TGFβ or activin yields dorsal types of mesoderm (Graff et al., 1996, Thomsen et al., 1996).

Figure 5A:
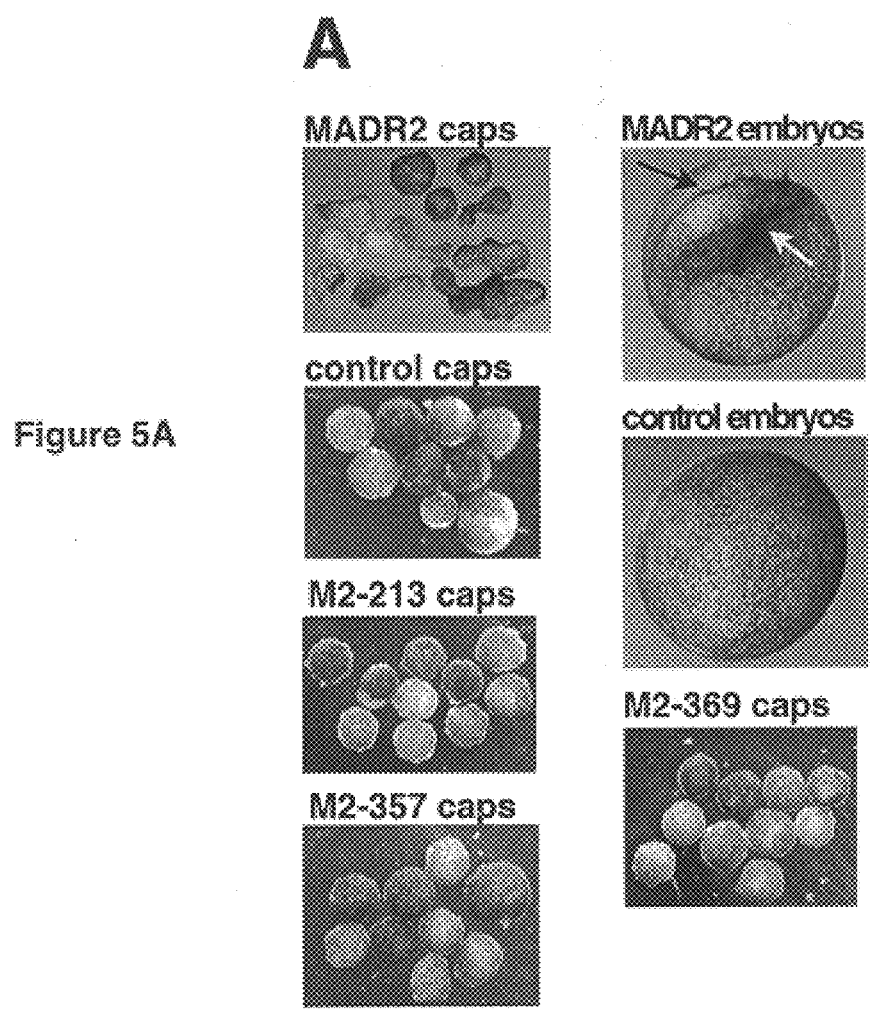
FIG. 5A shows the induction of morphogenetic movements and mesoderm by wild-type but not mutant MADR2 proteins. Animal caps cut from embryos injected with wild-type MADR2 elongated as they underwent morphogenetic movements associated with mesoderm differentiation, but control caps and caps expressing mutant MADR2 proteins did not. A representative control embryo is shown, which was indistinguishable from embryos that expressed the mutant forms of MADR2. An embryo expressing wild-type MADR2 showed an additional invagination furrow (white arrow) whose time of appearance coincided with the formation of the dorsal lip of the Spemann organizer, the normal site of gastrulation initiation. The normal gastrulation furrow (black arrow) of the illustrated embryo was displaced from its usual, more vegetal, position because of the action of the ectopic furrow. All wild-type MADR2-injected embryos were siblings of those used in the animal cap assays in B, all of which expressed MADR2 proteins.

Since the protein sequence of human MADR2 is 98% identical to Xmad2, the effect of MADR2 expression in Xenopus embryos was examined. MADR2 induced mesoderm and triggered morphogenic movements in a fashion similar to Xmad2 (FIG. 5). Expression of MADR2 from microinjected mRNA caused Xenopus ectoderm explants, or animal caps, to elongate (FIG. 5A) in response to treatment with TGFβ (Bhushan et al., 1994). These shape changes are considered to reflect the cellular movements that normally occur in the dorsal embryonic mesoderm during gastrula and neurula stages. MADR2 also triggered ectopic gastrulation movements in the ectoderm of intact embryos (FIG. 5A) precisely at the time normal gastrulation movements begin on the dorsal side of the embryo in the Spemann organizer. The MADR2 mutants 213, 357 and 369 did not cause animal caps to elongate or produce ectopic gastrulation movements in embryos, suggesting that the mutant proteins were functionally inactive.

Figure 5B:
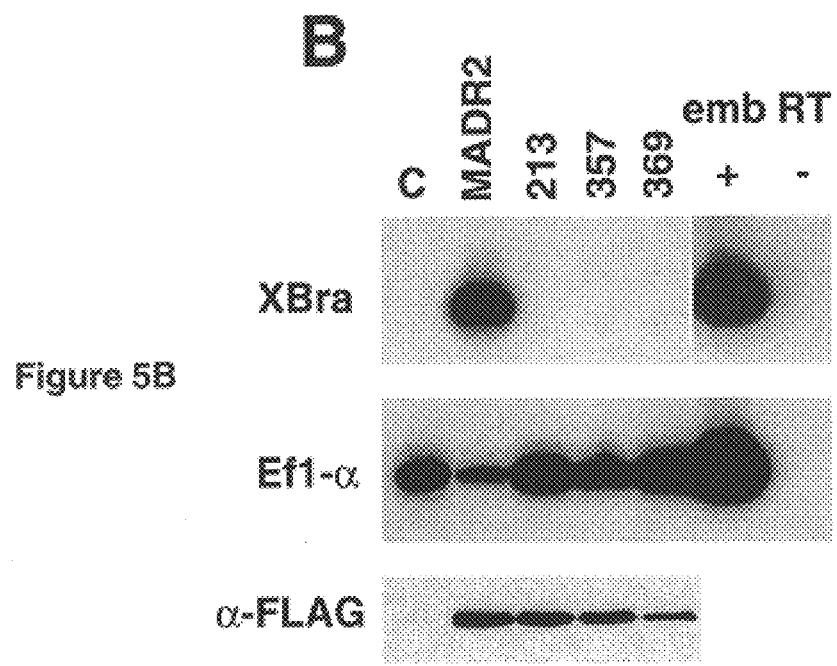
FIG. 5B shows RT-PCR analysis on animal caps injected with wild-type and mutated MADR2 mRNAs and showed that only wild type, and not mutated, MADR2 induced mesoderm as scored by the expression of brachyury, a general mesoderm marker at early to mid-gastrulation. Caps were injected with control (C;pGEM vector transcripts) and wild-type or mutant MADR2 mRNAs as indicated. EF1-α expression was scored as a general marker for RNA recovery. The emb RT + and − lanes were positive and negative controls using total embryonic RNA that was (+) or was not (−) reverse transcribed. A western blot of animal cap proteins stained with an anti-FLAG antibody is shown in the lower panel.

Wild-type and mutant MADR2 proteins were also tested for their capacity to induce mesoderm in animal caps. Wild-type MADR2 induced strong expression of the general mesodermal marker gene, brachyury (Xbra) (Smith et al., 1991) but the mutants did not (FIG. 5B). The lack of activity observed for the MADR2 mutants was not due to a lack of protein expression as western blot analysis of MADR2 protein expression in injected animal caps showed that wild type and mutant MADR2 were produced at nearly equal levels, except for 369, which was expressed at lower levels consistent with its apparent instability in mammalian tissue culture cells. These observations demonstrate that the mutations detected in colorectal tumors disrupt regulation by the TGFβ signalling pathway and yield biologically inactive MADR2 protein.

The Role of the Missense Mutations on MADR2 Function

TGFβ is a potent antiproliferative factor for a broad range of epithelial cells. The inactivating mutations identified in MADR2 likely disrupt TGFβ signalling, resulting in a loss of TGFP sensitivity in the target cells. This would give neoplastic clones a growth advantage in the tissue. However, there may be greater implications for the loss of TGFβ sensitivity in tumorigenesis. Malignant cancers are generally considered to be the result of a complex series of genetic and phenotypic changes (Clarke, 1991; Vogelstein et al., 1988). Neoplastic clones accumulate mutations which allow them not only to circumvent antiproliferative signals, but also to escape immune surveillance, initiate vascularization of the tumour and penetrate surrounding tissues by digestion of the extracellular matrix. Since TGFβ can function to regulate many of these events, disruption of normal responses to TGFβ, concomitant with increased secretion of the factor, may allow neoplastic cells to regulate their surroundings to promote development of the tumour (Roberts and Sporn 1993). These secondary events may be major contributing factors in the development of cancer and suggest additional mechanisms whereby loss of MADR2 and subsequent loss of responsiveness to TGFβ may contribute to malignancy.

The Mechanism of Interaction of MADR2 with TβRI and TβRII Receptors

To investigate whether a physiological substrate of the TGF-B complex might transiently interact with TβRI required the use of a catalytically inactive kinase to trap the substrate. FlagMADR2 was transiently expressed together with wild type TβII and either wild type TβRI or its kinase-deficient version. Receptors were visualized by affinity-labelling with [$^{125}$I]TGFβ and association assessed by analyzing the coprecipitation of receptors with MADR2. Analysis of MADR2 immunoprecipitates prepared from cells expressing wild type receptors revealed that no coprecipitating receptors were detected (FIG. 5). In contrast, the cells expressing wild type TβRII and kinase-deficient TβRI receptor complexes could clearly be detected coprecipitating with MADR2 protein. These findings strongly suggest that MADR2 transiently interacts with the TGFβ receptor through its interaction with the type I kinase.

It was demonstrated that transphosphorylation of receptor I by receptor II was essential to initiate signalling. It was then investigated whether activation of TβRI by TβRII was required for association of MADR2 with the receptor complex. MADR2 was cotransfected together with various wild type and kinase deficient versions of the type II and type I receptors in order to assess the association of MADR2 with TGFβ receptor complexes. While receptor complexes containing wild type TβRII and kinase deficient TβRI coprecipitated with MADR2, no association was detected between MADR2 and receptor complexes containing kinase defective type II receptors (FIG. 5B). Since this mutation specifically abolishes transphosphorylation of the type I receptor, these data indicated that activation of TβRI by TβRII was required for the association of MADR2 with the receptor complex.

Figure 6A:
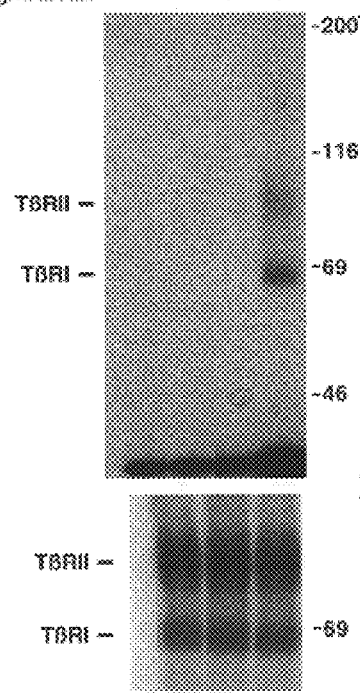
FIG. 6A is an autoradiograph showing the interaction of MADR2 with TGFβ receptors. COS-1 cells transiently transfected with empty vector (−) or FlagMADR2 and the indicated combinations of wild type (WT) or kinase deficient (KR) TβRI and HA-tagged TβRII were affinity labelled and the cell lysates immunoprecipitated to isolate receptor complexes which were visualized by SDS-PAGE and autoradiography. Total cell lysates shown in the bottom panel were analysed by SDS-PAGE.

The transient nature of the interaction of MADR2 with the TGFβ receptors and the ability of the kinase defective type I receptor to stabilize this association strongly suggested that MADR2 is a substrate for the ligand-activated type I receptor. It was then investigated whether bacterially expressed MADR2 could function as a substrate for the purified TGFβ receptor complex in an in vitro kinase assay. TGFβ receptors were isolated from either R1B/L17 cells (Carcmo et al, 1994) transiently transfected with TβRII and TβRI or from Mv1Lu cells expressing endogenous receptors. To drive formation of receptor complexes, cells were treated briefly with TGFβ and receptors purified from cell lysates using antibodies directed against TβRII. Immunoprecipitates were then subjected to an in vitro kinase assay using bacterially expressed MADR2 as a substrate. In both Mv1Lu and transiently transfected R1B/L17 cells only basal levels of MADR2 phosphorylation were observed when type II receptors were isolated in the absence of TGF-β addition (FIG. 6A). However, pretreatment of the cells with TGFβ for 30 min, which yields maximal heteromeric receptor complex formation (Wrna et al., 1994), resulted in a dramatic increase in the phosphorylation of MADR2 by the receptor complex. These results demonstrated that MADR2 is not a substrate of TβRII alone and its recognition and phosphorylation required ligand-induced assembly of the heteromeric receptor complex.

Figure 6B:
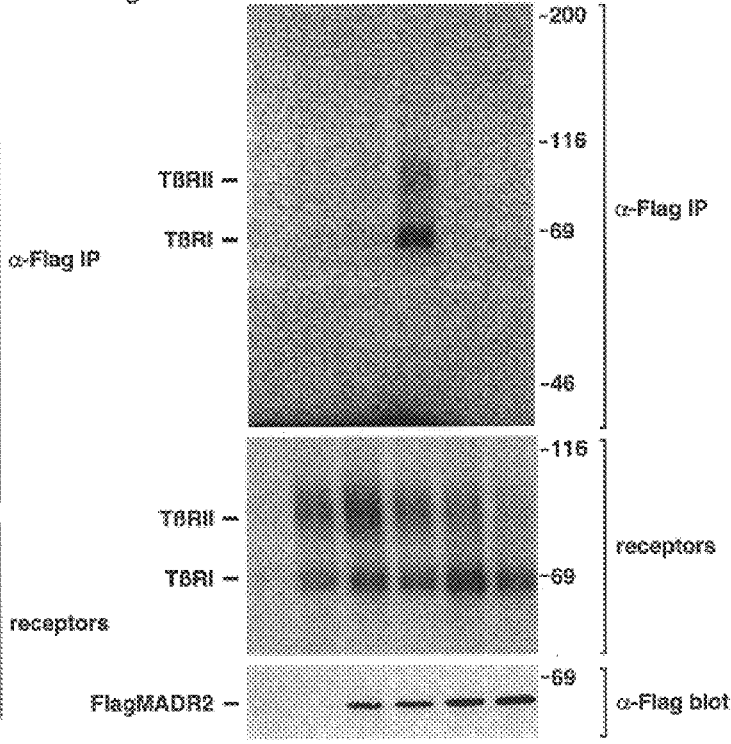
FIG. 6B is an autoradiograph showing MADR2 interaction with activated TGF-β receptor complexes. COS-1 cells transfected with FlagMADR2 and the indicated receptor constructs, were as described in FIG. 1A. The bottom panel shows the equivalent expression of FlagMADR2 protein determined by immunoblotting total cell lysates using anti-Flag M2 antibodies.

Tryptic phosphopeptide mapping was carried out to determine whether the in vitro phosphorylation mapped to the same sites on MADR2 as those phosphorylated by activation of TGFβ signalling in vivo. COS-1 cells which express higher levels of protein were utilized and phosphorylated MADR2 was generated from these cells by cotransfection of MADR2 with either wild type TβRI as a control or with constitutively active TβRI (Hoodless et al., 1996, Eppert 1996), which signals TGFβ responses in the absence of ligand (Wieser et al, 1995). While the basal phosphorylation of MADR2 in vivo occurred on a number of tryptic phosphopeptides (FIG. 6B), in the presence of the activated TGFβ receptor a single novel phosphopeptide that migrated towards the anode was distinguished. Maps prepared from in vitro phosphorylated MADR2 also showed nonspecific basal phosphorylation of the protein in reactions containing TβRII alone. However, in the presence of TβRII and TβRI a novel phosphopeptide was detected that appeared to comigrate with the TGFβ-dependent phosphopeptide identified in vivo (FIG. 6C). An additional phosphopeptide in the in vitro maps which migrated on a diagonal with the peptide observed in vivo was also observed (see FIG. 6 and 7) and may represent a phosphoisomer that is incompletely phosphorylated in the in vitro reactions (Boyle et al., 1991). To confirm that in vitro phosphorylation was the same as that observed in vivo, a mixture of tryptic fragments of MADR2 phosphorylated under both conditions was analyzed. Mapping of this sample demonstrated comigration of the phosphopeptides. Phosphoamino acid analysis of in vitro and in vivo labelled MADR2 revealed that phosphorylation occurred predominantly on serine residues with trace amounts of phosphothreonine also detected (data not shown). These mapping data indicate that phosphorylation in vitro by purified receptors mimics phosphorylation observed in vivo and suggest that MADR2 is a direct substrate of the heteromeric TGFβ receptor complex in vivo.

To determine the requirements for phosphorylation of MADR2 by the TGFβ receptor, receptor complexes from cells transfected with various combinations of wild type or kinase deficient receptors were isolated. For these studies COS-1 cells were utilized which contain low levels of TGFβ receptors and thus provide little endogenous background of wild type receptors. As already described, MADR2 was not phosphorylated by TβRII alone but was strongly phosphorylated by immunoprecipitates containing TβRII and TβRI. In contrast, in cells cotransfected with kinase deficient TβRI and wild type TβRII, no increase in phosphorylation of MADR2 was observed (FIG. 7A). Futher, immunoprecipitates containing kinase-deficient TβRII and wild type TβRI also failed to phosphorylate MADR2. Phosphopeptide mapping further confirmed that specific phosphorylation of MADR2 only occurred using wild type TGFβ receptors (FIG. 7B). These studies describing MADR2 phosphorylation in vitro and in vivo, together with the analysis of receptor association, strongly suggested that MADR2 is a direct substrate of the TGFβ receptor complex, is phosphorylated by the receptor I kinase and that this activity requires transphosphorylation of receptor I by receptor II.

Figure 8A:
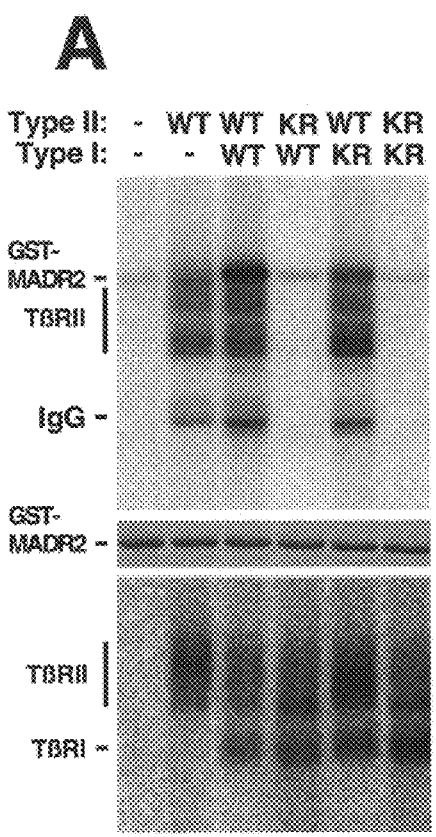
FIG. 8A is an autoradiograph showing the phosphorylation of MADR2 in vitro by wild type and kinase deficient receptor complexes. COS-1 cells were transiently transfected with empty vector (−) or with combinations of wild type (WT) and kinase deficient (KR) forms of TβRI and HA-tagged TβRII. Cells were incubated with TGFβ, lysed and receptor complexes were incubated in kinase assay buffer containing [$\gamma^{32}P$]ATP and bacterially expressed MADR2 fusion protein (GST-MADR2) as substrate. MADR2 phosphorylation was visualized by SDS-PAGE and autoradiography. The middle panel shows a Coomassie stained gel indicating constant levels of MADR2 protein. The bottom panel shows the amounts of receptor complex present in the kinase assays. The receptors were immunoprecipitated with anti-HA antibody. The migration of TβRII and TβRI is indicated.
Figure 8B:
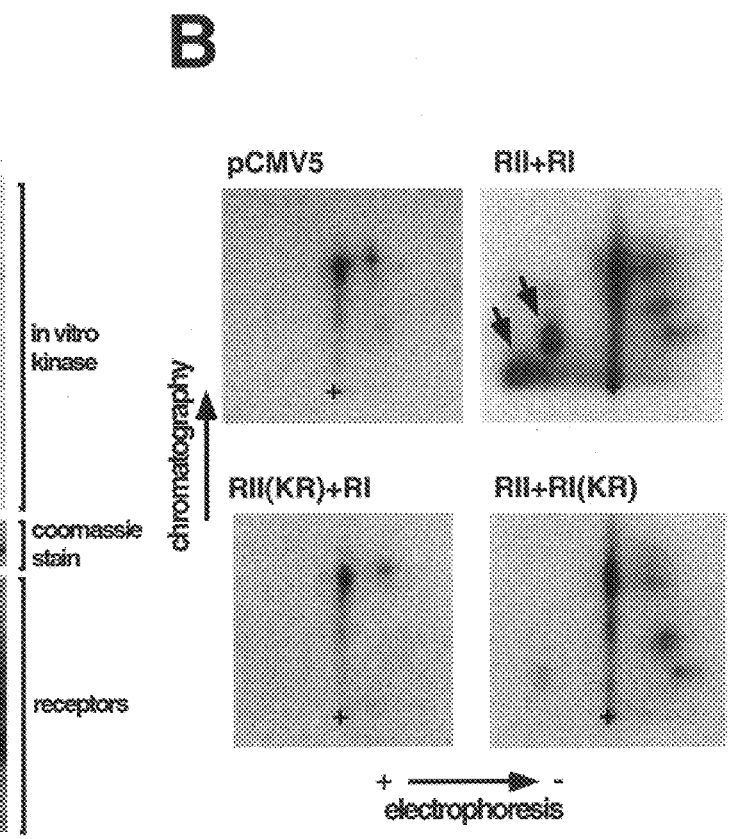
FIG. 8B shows mapping of tryptic digests of gelpurified MADR2, by resolution in two dimensions and visualization by autoradiography. The relevant phosphopeptides (arrows) and the location of the sample application (+) are indicated.

To determine the specificity of MADR interactions with the TGFβ receptor, the MAD-related protein, DPC4 was analyzed. DPC4 was first identified as a tumour suppressor gene in pancreatic carcinoma (Hahn et al., 1996) and is not phosphorylated in response to TGFβ. MADR immunoprecipitates were prepared from [$^{125}$I]TGFβ affinity-labelled cells coexpressing TβRII and kinase deficient TβRI together with either MADR2 or DPC4. While receptor complexes were detected in MADR2 immunoprecipitates, no receptors coprecipitating with DPC4 were observed (FIG. 8A). Similarly, in vitro kinase asays showed that TGFβ receptors were capable of phosphorylating bacterially expressed MADR2 but not DPC4 (FIG. 8B). Thus, MADR2, and not another related MADR, specifically associates with and becomes phosphorylated by the TGFβ receptors.

The studies have demonstrated that MADR2 associates with the TGFβ receptor complex and that this association requires transphosphorylation of the type I receptor by the type II receptor (FIG. 8C). Further, it has been demonstrated that MADR2 is a direct substrate of the TGFβ receptor, that phosphorylation is catalyzed by the type I receptor kinase and that this activity requires activation of receptor I by receptor II. The association and phosphorylation is specific, since the MAD-related protein, DPC-4 did not associate with nor was phosphorylated by the TGFβ receptor. These results, together with the recent demonstration that MADRs accumulate in the nucleus (Hoodless et al., 1996, Liu et al., 1996) and may act as transcriptional activators (Liu et al., 1996), suggest a model for MADR function in TGFβ signalling. Ligand-induced receptor complex formation results in receptor II mediated activation of receptor I which is then recognized by MADR2. MADR2 transiently associates with the receptor, but dissociates upon phosphorylation and may then move to the nucleus to carry out its effector functions (FIG. 8C). Thus MADRs, as the physiological substrates of serine threonine kinase receptors, may transmit signals directly from the receptor into the nucleus.

Transcriptional factors bind to specific regulatory sites on the DNA to stimulate transcription, although in some cases, transcription factors may in fact repress transcription. In order to determine whether MADR2 is a transcription factor, one could determine whether the MADR2 protein binds to a region of DNA by Dnase I footprinting. In this technique, a region of DNA that is bound to a protein is protected from digestion with DNase I. When DNA samples digested in the presence and absence of a DNA-binding protein are electrophoresed, the region protected by the bound protein appears as a gap or "footprint" in the array of bands resulting from digestion in the absence of protein. The products of DNA sequencing reactions of the DNA sample being footprinted generally are analyzed on the same gel in order to determine the precise sequence protected from DNase I digestion by the bound protein.

DNA-binding by proteins can be measured quantitatively with the electrophoretic mobility shift assay (gel-shift, bandshift). In this assay the electrophoretic mobility of a radio-labelled DNA fragment is determined in the presence and absence of a sequence-specific DNA-binding protein causing a shift in the location of the fragment band detected by auto radiography. Purification of a DNA-binding protein can be carried out by column chromatography such as sequence-specific DNA affinity chromatography.

Transcription rates between cells transfected with wild-type MADR1 and mutated MADR2 can also be assayed to determine what effects mutations in the gene sequence, especially in the MH1 and MH2 domains, have on the transcription of DNA. MADR2 has been demonstrated to have transcriptonal activity in yeast. Transcription rates can be measured in cultured cells by exposing the cells for a brief period to a labelled RNA precursor and then determining the amount of labelled nuclear RNA formed by its hybridization to cloned DNA. Nascent-chain or run-on analysis is another method which can be used to measure transcription rates. In this method, nuclei are isolated from cells and allowed to incorporate $^{32}P$ from labelled ribonucleoside triphosphates directly into nascent RNA chains to produce highly labelled RNA preparations. Reactions are run for a brief period so that the RNA polymerace adds 300–500 nucleotides to nascent RNA chains. By hybridizing the labelled RNA to cloned DNA from a specific gene, the fraction of the total RNA copied from a particular gene, i.e. its relative transcription rate, can be determined.

MADR2 does not resemble the structural motifs of other transcriptional factors and for this reason, it is possible that the protein does not directly activate transcription. MADR2 could target other proteins and in this manner affect transcription by complex protein-protein interactions involving other DNA-binding protein(s).

MADR2 could act as an adaptor protein to bring together two other protein molecules by the binding of proteins to each domain, MH1 and MH2. These proteins may then directly or indirectly, through protein-protein interactions, affect the transcription of certain genes. Phosphorylation of MADR2 could alter the structure of the MADR2 protein leading to the recognition of specific proteins such as DNA-binding and transcriptional activators, and in this manner affect DNA transcription.

Isolation and Purification of MADR2 Protein

Both human and mouse MADR2 proteins, fragments of the proteins and fusion proteins may be isolated and purified by techniques well known to those skilled in the art. The MADR2 protein may be purified from tissues (e.g. gastrointestinal tract) in which there is a high level of expression of the protein or it may be made by recombinant techniques. Isolated proteins, or fragments thereof can be used for the generation of antibodies, in the identification of proteins which may bind to hMADR2 or mMADR2 or fordiagnostic or therapeutic methods and assays. Full length proteins and fragments of at least 4 amino acids may be isolated and purified for various applications The protein may be isolated from tissue by extraction and solubilized using a detergent.

Purification can be achieved using protein purification procedures such as chromatography methods (gel-filtration, ion-exchange and immunoaffinity), by high-performance liquid chromatography (RP-HPLC, ion-exchange HPLC, size-exclusion HPLC, high-performance chromatofocusing and hydrophobic interaction chromatography) or by precipitation (immunoprecipitation or immunoaffinity SDS-Page and Page). Polyacrylamide gel electrophoresis can also be used to isolate the MADR2 protein based on its molecular weight, charge properties and hydrophobicity.

Similar procedures may be used to purify the protein from recombinant expression system.

For protein expression, eukaryotic or prokaryotic expression systems may be generated in which the MADR2 gene sequence, cDNA or genomic, is introduced into a plasmid or other expression vector which is then introduced into living cells. Constructs in which the MADR2 cDNA sequence containing the entire open reading frame inserted in the correct orientation into an expression plasmid may be used for protein expression. Alternatively, portions of the normal or mutant MADR2 sequences may be inserted.

Typical expression vectors contain promoters that direct the synthesis of large amounts of mRNA corresponding to the gene. They may also include sequences allowing for their autonomous replication within the host organism, sequences that encode genetic traits that allow cells containing the vectors to be selected, and sequences that increase the efficiency with which the mRNA is translated. Stable long-term vectors may be maintained as freely replicating entities by using regulatory elements of viruses. Cell lines may also be produced which have integrated the vector into the genomic DNA and in this manner the gene product is produced on a continuous basis.

Expression of foreign sequences in bacteria such as *E. coli* require the insertion of the sequence into an expression vector, usually a plasmid which contains several elements such as sequences encoding a selectable marker that assures maintenance of the vector in the cell, a controllable transcriptional promoter which upon induction can produce large amounts of mRNA from the cloned gene, translational control sequences and a polylinker to simplify insertion of the gene in the correct orientation within the vector. A relatively simple *E. coli* expression system utilizes the lac promoter and a neighbouring lacZ gene which is cut out of the expression vector with restriction enzymes and replaced by the MADR2 gene sequence.

In vitro expression of proteins encoded by cloned DNA is also possible using the T7 late-promoter expression system. Plasmid vectors containing late promoters and the corresponding RNA polymerases from related bacteriophages such as T3, T5 and SP6 may also be used for in vitro production of proteins from cloned DNA. *E. coli* can also be used for expression by infection with M13 Phage mGPI-2. *E. coli* vectors can also be used with phage lambda regulatory sequences, with fusion protein vectors, with maltose-binding protein fusions, and with glutathione-S-transferase fusion proteins.

Eukaryotic expression systems permit appropriate post-translational modifications of expressed proteins. This allows for studies of the MADR2 gene and gene product including determination of proper expression and post-translational modifications for biological activity, identifying regulatory elements in the 5' region of the gene and their role in tissue regulation of protein expression. It also permits the production of large amounts of normal and mutant proteins for isolation and purification, the use of cells expressing MADR2 as a functional assay system for antibodies generated against the protein, the testing of the effectiveness of pharmacological agents or to increase or decrease the activity of MADR2, and the study of the function of the normal complete protein, specific portions of the protein, or of naturally occurring polymorphisms and artificially produced mutated proteins.

In order to produce mutated or polymorphic proteins, the MADR2 DNA sequence can be altered using procedures such as restriction enzyme digestion, DNA polymerase fill-in, exonuclease deletion, terminal deoxynucleotide transferase extension, ligation of synthetic or cloned DNA sequences and site-directed sequence alteration using specific oligonucleotides together with PCR. Alteration of the cDNA will allow for the production of specific mutations within cDNA sequence in order to express the created mutated proteins and study their biological effects.

Once an appropriate expression vector containing the MADR2 gene is constructed, it is introduced into an appropriate *E. coli* strain by transformation techniques including calcium phosphate transfection, DEAE-dextran transfection, electroporation, microinjection, protoplast fusion and liposome-mediated transfection.

The host cell to be transfected with the vector of this invention may be selected from the group consisting of E.coli, Pseudomonas, Bacillus Subtilis, or other bacilli, other bacteria, yeast, fungi, insect (using baculoviral vectors for expression), mouse or other animal or human tissue cells. Mammalian cells can also be used to express the MADR2 protein using a vaccinia virus expression system.

Prokaryotic and eukaryotic expression systems allow various important functional domains of the protein to be recovered as fusion proteins and used for binding, structural and functional studies and also for the generation of appropriate antibodies.

In order to express and purify the protein as a fusion protein, the MADR2 cDNA sequence is inserted into a vector which contains a nucleotide sequence encoding another peptide (eg. GST—glutathionine succinyl transferase). The fusion protein is expressed and recovered from prokaryotic (eg. bacterial or baculovirus) or eukaryotic cells. The fusion protein can then be purified by affinity chromatography based upon the fusion vector sequence and the MADR2 protein obtained by enzymatic cleavage of the fusion protein.

Fusion proteins are particularly advantageous because they provide a system for ensuring a good expression of the protein without making any alternations to the 5' end of the coding sequence or immediately preceding the start codon.

In the fusion approach, a cloned gene is introduced into an expression vector 3' to a carrier sequence coding for the amino terminus of a highly expressed protein. The carrier sequence provides the necessary signals for good expression and the expressed fusion protein contains a N terminal region encoded by the carrier.

Purified protein can also be used in further biochemical analyses to establish secondary and tertiary structure. The preparation of substantially purified MADR2 protein or fragments thereof allows for the determination of the protein tertiary structure by x-ray crystallography of crystal of MADR2 protein or by NMR. Determination of structure may aid in the design of pharmaceuticals to interact with the protein, alter protein charge configuration or charge interaction with other proteins, or to alter its function in the cell.

Antibodies

The knowledge of the amino acid and nucleotide sequence of the human and mouse MADR2 allows for the production of antibodies which selectively bind the MADR2 protein or fragments thereof. With the identification of mutations in the MADR2 sequence, antibodies can also be made to selectively bind and/or distinguish mutant from normal protein.

In order to prepare polyclonal antibodies, fusion proteins containing defined portions or all of the MADR2 protein can be synthesized in bacteria by expression of corresponding DNA sequences in a suitable cloning vehicle. Fusion proteins are commonly used as a source of antigen for producing antibodies. Alternatively protein may be isolated and purified from MADR2 expressing cultures and used as a source of antigen. It is understood that the entire protein or fragments thereof can be used as a source of antigen to produce antibodies.

The purified MADR2 protein is purified, coupled to a carrier protein and mixed with Freund's adjuvant (to help stimulate the antigenic response by the animal) and injected into rabbits or other appropriate laboratory animals. Following booster injections at weekly intervals, the rabbits or other laboratory animals are then bled and the sera isolated. The sera can be used directly or purified prior to use by various methods including affinity chromatography employing Protein A-Sepharose, Antigen Sepharose or Anti-mouse-Ig-Sepharose, to give polyclonal antibodies.

Alternatively, synthetic peptides can be made corresponding to the antigenic portions of the protein, and used to inoculate the animals.

The most common practice is to choose a 10 to 15 amino acid residue peptide corresponding to the carboxyl or amino terminal sequence of a protein antigen, and to chemically cross-link it to a carrier molecule such as keyhole limpet hemocyanin or BSA. However, if an internal sequence peptide is desired, selection of the peptide is based on the use of algorithms that predict potential antigenic sites. These predictive methods are, in turn, based on predictions of hydrophilicity (Kyte and Doolittle 1982, Hopp and Woods 1983) or secondary structure (Chou and Fasman 1978). The objective is to choose a region of the protein that is either surface exposed, such as a hydrophilic region, or is conformationally flexible relative to the rest of the structure, such as a loop region or a region predicted to form a β-turn. The selection process is also limited by constraints imposed by the chemistry of the coupling procedures used to attach peptide to carrier protein. Carboxyl-terminal peptides are frequently chosen because these are often more mobile than the rest of the molecule and the peptide can be coupled to a carrier in a straightforward manner using glutaraldehyde. The amino-terminal peptide has the disadvantage that it may be modified post-translationally by acetylation or by the removal of a leader sequence. A comparison of the protein amino acid sequence between species can yield important information. Those regions with sequence differences between species are likely to be immunogenic. Synthetic peptides can also be synthesized as immunogens as long as they mimic the native antigen as closely as possible.

It is understood by those skilled in the art that monoclonal MADR2 antibodies may also be produced. MADR2 protein isolated from tissues, or from cells recombinantly expressing the protein, is injected in Freund's adjuvant into mice. Mice are injected 9 times over a three week period, after which their spleens are removed and resuspended in phosphate buffered saline (PBS). The spleen cells serve as a source of lymphocytes, some of which are producing antibody of a selected specificity. These are then fused with a permanently growing myeloma partner cell, and the products of the fusion are plated into a number of tissue culture wells in the presence of a selective agent such as HAT. The wells are then screened by ELISA to identify those containing cells making binding antibody. These are then plated and after a period of growth, these wells are again screened to identify antibody-producing cells. Several cloning procedures are carried out until over 90% of the wells contain single clones which are positive for production of the desired antibody. From this procedure, a stable line of clones which produce the antibody is established. The monoclonal antibody can then be purified by affinity chromatography using Protein A Sepharose, ion-exchange chromatography, as well as variations and combinations of these techniques. Truncated versions of monoclonal antibodies may also be produced by recombinant techniques in which plasmids are generated which express the desired monoclonal antibody fragment(s) in a suitable host.

Antibodies specific for mutagenised epitopes can also be generated. These antibodies are especially useful in cell culture assays to screen for malignant cells at different stages of malignant development. Such antibodies are also useful for screening malignant cells which have been treated with pharmaceutical agents in order to evaluate the therapeutic potential of the pharmaceutical agent. MADR2 antibodies are also useful for detecting both normal and mutant proteins in cell culture, and transfected cell cultures expressing normal or mutant MADR2 protein as well as for western blot analysis on protein extracts of such cells.

Antibodies are also useful in various immunoassays for detecting and quantitating relative amounts of wild type and mutant protein. Enzyme-linked immunosorbant assays (ELISA) may be used to detect both wild type and mutant MADR2 as well as antibodies generated against these proteins. Commonly used ELISA systems are indirect ELISA to detect specific antibodies, direct competitive ELISA to detect soluble antigens, antibody-sandwich ELISA to detect coluble antigens and double antibody-sandwich ELISA to detect specific antibodies.

Antibodies to MADR2 may also be used for coupling to compounds such as radionuclides or fluorescent compounds, or to liposomes for diagnostic imaging and therapy, in order to target compounds to a specific tissue location. This is especially valuable for the specific targeting of malignant tissues with anti-cancer drugs, which would be detrimental to normal cells and tissues.

For a review of methods for preparation of antibodies, see *Antibody Engineering: A Practical Guide*, Barreback, ed., W. H. Freeman & Company, N.Y. (1992) or *Antibody Engineering*, 2nd Ed., Barreback, ed., Oxford University Press, Oxford (1995).

Cellular Distribution of MADR2 in Malignant and Normal Tissues

The cellular distribution of MADR2 in malignant and normal tissues may be analyzed by reverse transcriptase PCR analysis. In order to define the cellular distribution of MADR2, antibodies can be raised against both normal and mutant MADR2 proteins, as well as to phosphorylated proteins. Such antibodies can then be used in both immunocytochemistry and immunofluorescence techniques to visualize the protein directly in cells and tissues in order to establish the subcellular location of normal and mutant proteins before and after stimulation with TGFβ.

In situ hybridization is another method which may be used to detect the expression of normal and mutant MADR2. In situ hybridization relies upon the hybridization of a specifically labelled nucleic acid probe to the cellular RNA in individual cells or tissues. Therefore, it allows the identification of mRNA within intact tissues. In this method, oligonucleotides corresponding to unique portions of the MADR2 gene, normal or mutant, are used to detect specific mRNA species in the tissue of interest. The animal is anesthetized and transcardially perfused with cold PBS, followed by perfusion with a formaldehyde solution. The tissue is then removed, frozen in liquid nitrogen, and cut into thin micron sections. The sections are placed on slides and incubated in proteinase K. Following rinsing in DEP, water and ethanol, the slides are placed in a prehybridization buffer. A radioactive probe corresponding to the primer is made by nick translation and incubated with the sectioned tissue. After incubation and air drying, the labeled areas are visualized by autoradiography. Dark spots on the tissue sample indicate hybridization of the probe with MADR2 mRNA which demonstrates the expression of the protein.

Isolated Nucleic Acids

In accordance with one series of embodiments, this invention provides isolated nucleic acids corresponding to the nucleic acid sequences encoding the human and mouse MADR2 genes. Also provided are mutant human sequences and portions of the normal and mutant MADR2 sequences useful as probes and PCR primers or for encoding fragments, functional domains or antigenic determinants of MADR2 proteins.

One of ordinary skill in the art is now enabled to identify and is isolate MADR2 genes or cDNAs which are allelic variants of the disclosed MADR2 sequences, using standard hybridization screening or PCR techniques.

Depending on the intended use, the invention provides portions of the disclosed nucleic acid sequences comprising about 10 consecutive nucleotides (e.g. for use as PCR primers) to nearly the complete disclosed nucleic acid sequences. The invention provides isolated nucleic acid sequences comprising sequences corresponding to at least 10, preferably 15 and more preferably at least 20 consecutive nucleotides of the MADR2 genes as disclosed or enabled herein or their complements.

In addition, the isolated nucleic acids of the invention include any of the above described nucleotide sequences included in a vector.

Substantially Pure Proteins

In accordance with a further series of embodiments, this invention provides substantially pure MADR2 proteins, fragments of these proteins and fusion proteins including these proteins and fragments.

The proteins, fragments and fusion proteins have utility, as described herein, for the preparation of polyclonal and monoclonal antibodies to normal and mutant MADR2 proteins, for the identification of binding partners of the MADR2 proteins and for diagnostic and therapeutic methods, as described herein. For these uses, the present invention provides substantially pure proteins, polypeptides or derivatives of polypeptides which comprise portions of the MADR2 amino acid sequences disclosed or enabled herein and which may vary from about 4 to 5 amino acids (e.g. for use as immunogens) to the complete amino acid sequence of the MADR2 proteins. The invention provides substantially pure proteins or polypeptides comprising sequences corresponding to at least 5, preferably at least 10 and more preferably 50 or 100 consecutive amino acids of the MADR2 proteins disclosed or enabled herein.

Screening and Diagnostic Mutant MADR2 in Malignancy

A. General Diagnostic Methods

The MADR2 gene and gene product, as well as the MADR2-derived probes, primers and antibodies, disclosed or otherwise enabled herein, are useful in the screening for carriers of alleles associated with colorectal carcinoma or related malignancies, for the diagnosis of victims of cancer, and for the screening and diagnosis of related malignancies, all of which are seen to a greater or lesser extent in symptomatic human subjects bearing mutations in the MADR2 gene. Individuals at risk for developing colorectal carcinoma possibly those with caner present in the family pedigree, or individuals not previously known to be at risk, may be routinely screened using probes to detect the presence of a mutant MADR2 gene or protein by a variety of techniques. Diagnosis of inherited cases of these diseases can be accomplished by methods based upon the nucleic acid (including genomic and mRNA/cDNA sequences), proteins, and/or antibodies disclosed and enabled herein, including functional assays designed to detect failure or augmentation of the normal MADR2 activity and/or the presence of specific new activities conferred by mutant MADR2. Preferably, the methods and products are based upon the human MADR2 nucleic acids, protein or antibodies, as disclosed or otherwise enabled herein. As well be obvious to one of ordinary skill in the art, however, the significant evolutionary conservation of large portions of the MADR2 nucleotide and amino acid sequence, even in species as diverse as humans, mice, and Drosophila, allow the skilled artisan to make use of such non-human MADR2-homologue nucleic acids, proteins and antibodies, even for applications directed toward human or other animal subjects. Thus, for brevity of exposition, but without limiting the scope of the invention, the following description will focus upon uses of the human homologies of MADR2. It will be understood, however, that homologous sequences from other species, including those disclosed herein, will be equivalent for many purposes.

As will be appreciated by one of ordinary skill in the art, the choice of diagnostic methods of the present invention will be influenced by the nature of the available biological samples to be tested and the nature of the information required. MADR2 is expressed in all tissues, however, in some tissues it is possible that MADR2 may be alternatively spliced which means that MADR2 mRNA or protein from such cells may be less informative. Thus, an assay based upon a subject's genomic MADR2 DNA may be preferred because no information will be dependent upon alternative splicing and because essentially any nucleate cells may provide a usable sample.

B. Protein Based Screens and Diagnostics

When a diagnostic assay is to be based upon the MADR2 protein, a variety of approaches are possible. For example, diagnosis can be achieved by monitoring differences in the electrophoretic mobility of normal and mutant proteins. Such an approach will be particularly useful in identifying mutants in which charge substitutions are present, or in which insertions, deletions or substitutions have resulted in a significant change in the electrophoretic migration of the resultant protein. Alternatively, diagnosis may be based upon differences in the proteolytic cleavage patterns of normal and mutant proteins, differences in molar ratios of the various amino acid residues, or by functional assays demonstrating altered function of the gene products.

In preferred embodiments, protein-based diagnostics will employ differences in the ability of antibodies to bind to normal and mutant MADR2 proteins. Such diagnostic tests may employ antibodies which bind to the normal proteins but not to mutant proteins, or vice versa. In particular, an assay in which a plurality of monoclonal antibodies, each capable of binding to a mutant epitope, may be employed. The levels of anti-mutant antibody binding in a sample obtained from a test subject (visualized by, for example, radiolabelling, ELISA or chemiluminescence) may be compared to the levels of binding to a control sample. Alternatively, antibodies which bind to normal but not mutant MADR2 may be employed, and decreases in the level of antibody binding may be used to distinguish homozygous normal individuals from mutant heterozygotes or homozygotes. Such antibody diagnostics may be used for in situ immunohistochemistry using biopsy samples of tissues obtained antemortem or postmortem. Also fluid samples such as cerebrospinal fluid or with peripheral tissues such as white blood cells.

C. Nucleic Acid Based Screens and Diagnostics

When the diagnostic assay is to be based upon nucleic acids from a sample, the assay may be based upon mRNA, cDNA or genomic DNA. When mRNA is used from a sample, many of the same considerations apply with respect to source tissues and the possibility of alternative splicing. Whether mRNA, cDNA or genomic DNA is assayed, standard methods well known in the art may be used to detect the presence of a particular sequence either in situ or in vitro (see, e.g., Sambrook et al., (1989) *Molecular Cloning: A Laboratory Manual*, 2nd ed., Cold Spring Harbor Press, Cold Spring Harbor, N.Y.). As a general matter, however, any tissue with nucleated cells may be examined.

Genomic DNA used for the diagnosis may be obtained from body cells, such as those present in the blood, tissue biopsy, surgical specimen, or autopsy material. The DNA may be isolated and used directly for detection of a specific sequence or may be amplified by the polymerase chain reaction (PCR) prior to analysis. Similarly, RNA or CDNA may also be used, with or without PCR amplification. To detect a specific nucleic acid sequence, direct nucleotide sequencing, hybridization using specific oligonucleotides, restriction enzyme digest and mapping, PCR mapping, RNase protection, chemical mismatch cleavage, ligase-mediated detection, and various other methods may be employed. Oligonucleotides specific to particular sequences can be chemically synthesized and labeled radioactively or nonradioactively (e.g., biotin tags, ethidium bromide), and hybridized to individual samples immobilized on membranes or other solid-supports (e.g., by dot-blot or transfer from gels after electrophoresis), or in solution. The presence or absence of the target sequences may then be visualized using methods such as autoradiography, fluorometry, or colorimetry. These procedures can be automated using redundant, short oligonucleotides of known sequence fixed in high density to silicon chips.

(1) Appropriate Probes and Primers

Whether for hybridization, RNase protection, ligase-mediated detection, PCR amplification or any other standards methods described herein and well known in the art, a variety of subsequences of the MADR2 sequences disclosed or otherwise enabled herein will be useful as probes and/or primers. These sequences or subsequences will include both normal MADR2 sequences and deleterious mutant sequences. In general, useful sequences will include at least 8–9, more preferably 10–50, and most preferably 18–24 consecutive nucleotides from the MADR2 introns, exons or intron/exon boundaries. Depending upon the target sequence, the specificity required, and future technological developments, shorter sequences may also have utility. Therefore, any MADR2 derived sequence which is employed to isolate, clone, amplify, identify or otherwise manipulate a MADR2 sequence may be regarded as an appropriate-probe or primer.

Particularly contemplated as useful will be sequences including nucleotide positions from the MADR2 genes in which disease-causing mutations are known to be present, or sequences which flank these positions. Particularly contemplated as useful are probes or primers derived from sequences encoding the MH1 and MH2 regions. However, mutations may be detected which affect other regions of the MADR2 protein and, using the methods disclosed herein, more will undoubtedly be detected. Therefore, the present invention provides isolated nucleic acid probes and primers corresponding to normal and mutant sequences from any portion of the MADR2 gene, including introns and 5' and 3' UTRS, which may be shown to be associated with the development of malignancy.

Merely as an example, and without limiting the invention, probes and primers derived from the MADR2 DNA segment immediately surrounding the P445H mutation may be employed in screening and diagnostic methods. This mutation arises, at least in some individuals, from the substitution of an A for a C at position 1371 of SEQ ID NO: 1. Thus, genomic DNA, mRNA or cDNA acquired from peripheral blood samples or tissue biopsies from an individual can be screened using oligonucleotide probes or primers including this potentially mutant site. For hybridization probes for this mutation, probes of 8–50, and more preferably 18–24 bases spanning the mutation site may be employed. If the probe is to be used with mRNA, it should of course be complementary to the mRNA (and, therefore, correspond to the non-coding strand of the MADR2 gene. For probes to be used with genomic DNA or cDNA, the probe may be complementary to either strand. To detect sequences including this mutation by PCR methods, appropriate primers would include sequences of 8–50, and preferably 18–24, nucleotides in length derived from the regions flanking the mutation on either side, and which correspond to positions anywhere from 1 to 1000 bp, but preferably 1–200 bp, removed from the site of the mutation. PCR primers which are 5' to the mutation site (on the coding strand) should correspond in sequence to the coding strand of the MADR2 gene whereas PCR primers which are 3' to the mutation site (on the coding strand) should correspond to the non-coding or antisense strand.

Similar primers may be chosen for other MADR2 mutations or for the mutational "hot spots" in general.

It should also be noted that the probes and primers may include specific mutated nucleotides. Thus, for example, a hybridization probe or 5' primer may be produced for the L440R mutation comprising a sequence corresponding to approximately bp of 1356–1374 SEQ ID NO: 1 to screen for or amplify normal alleles, or corresponding to the same sequence but with the bp corresponding to the altered base pair to screen for or amplify mutant alleles.

Methods of Treatment

Therapies may be designed to circumvent or overcome a MADR2 gene defect or inadequate MADR2 gene expression, and thus moderate and possibly prevent malignancy. The MADR2 gene has been found to be mutated in colorectal carcinomas. In considering various therapies, however, it is understood that such therapies may be targeted at other malignant tissues demonstrated to express mutant MADR2.

Protein Therapy

Treatment or prevention of colorectal and other cancers can be accomplished by replacing the mutant MADR2 protein with normal protein, by modulating the function of mutant protein, or by delivering normal MADR2 protein to the appropriate cells. Alternatively, phosphorylated protein may also be used to replace mutated protein, since it has been demonstrated that MADR2 phosphorylation is required for normal function. Once the biological pathway involving the MADR2 protein has been completely elucidated and understood, it may also be possible to modify the pathophysiologic pathway (signal transduction pathway involving phosphorylation) in which the protein participates in order to correct the physiological defect.

To replace a mutant protein with normal protein, or to add protein to cells which no longer express normal MADR2, it is necessary to obtain large amounts of pure MADR2 protein from cultured cell systems which can express the protein. Delivery of the protein to the affected cells and tissues can then be accomplished using appropriate packaging or administration systems. Alternatively, small molecule analogs may be used and administered to act as MADR2 agonists or antagonists and in this manner produce a desired physiological effect. In order to screen for analogues, one can design functional screens based on the sequence of MADR2. One can also fuse MADR2 to heterologous DNA binding proteins to design screens for agonists. Since MADR2 functions by interacting with other proteins, yeast screens can be used for small molecules that may interact by promoting or disrupting MADR2 binding with other proteins.

Based on the biochemical analyses of MADR2 protein structure-function, one can design drugs to mimic the effects of phosphorylated MADR2 on target proteins.

The clone of MADR2 expressed as a fusion protein can be utilized to identify small peptides that bind to MADR2. In one approach, termed phage display, random peptides (up to 20 amino acids long) are expressed with coat proteins (geneIII or geneVIII) of filamentous phage such that they are expressed on the surface of the phage thus generating a library of phage that express random sequences. A library of these random sequences is then selected by incubating the library with the MADR2 protein or fragments thereof and phage that bind to the protein are then eluted either by cleavage of MADR2 from the support matrix or by elution using an excess concentration of soluble MADR2 protein or fragments. The eluted phage are then repropagated and the selection repeated many times to enrich for higher affinity interactions. The random peptides can either by completely random or constrained at certain positions through the introduction of specific residues. After several rounds of selection,t he final positive phage are sequenced to determine the sequence of the peptide.

An alternate but related approach uses the yeast two hybrid system to identify binding partners for MADR2. MADR2 or fragments are expressed in yeast as a fusion to a DNA binding domain. This fusion protein is capable of binding to target promoter elements in genes that have been engineered into the yeast. These promoters drive expression of specific reporter genes (Typically the auxotrophic marker HIS3 and the enzyme βgalactosidase). A library of cDNAs can then be constructed from any tissue or cell line and fused to a transcriptional activation domain. Transcription of HIS3 and β-galactosidase depends on association of the MADR2 fusion protein (which contains the DNA binding domain) and the target protein (which carries the activation domain). Yeast survival on specific growth media lacking histidine requires this interaction. This approach allows for the identification of specific proteins that interact with MADR2. The approach has also been adapted to identify small peptides. MADR2, or its fragments, are fused with the DNA binding domain and are screened with a library of random peptides or peptides which are constrained at specific positions linked to a transcriptional activation domain. Interaction is detected by growth of the interacting peptides on media lacking histidine and by detection of β-galactosidase activity using standard techniques.

The identification of proteins or small peptides that interact with MADR2 can provide the basis for the design of small peptide antagonists or agonists of MADR2 function. Further, the structure of these peptides determined by standard techniques such as protein NMR or X-ray crystallography can provide the structural basis for the design of small molecule drugs.

Gene Therapy

Gene therapy is another potential therapeutic approach in which normal copies of the MADR2 gene are introduced into selected tissues to successfully code for normal protein in affected cell types. It is to be understood that gene therapy techniques can only begin once a malignant genotype/phenotype has been identified. The gene must be delivered to affected cells in a form in which it can be taken up and can code for sufficient protein to provide effective function. Alternatively, in some mutants, it may be possible to prevent malignancy by introducing another copy of the homologous gene bearing a second mutation in that gene, or to alter the mutation, or to use another gene to block any negative effect.

Transducing retroviral vectors can be used for somatic cell gene therapy especially because of their high efficiency of infection and stable integration and expression. The targeted cells must be able to divide and the expression level of normal protein should be high. The full length MADR2 gene, or portions thereof, can be cloned into a retroviral vector and driven from its endogenous promoter or from the retroviral long terminal repeat or from a promoter specific for the target cell type of interest. Other viral vectors which can be used include adeno-associated virus, vaccinia virus, bovine papilloma virus, or a herpes virus such as Epstein-Barr virus.

Gene transfer could also be achieved using non-viral methods of infection in vitro. These methods would include calcium phosphate, DEAE dextran, electroporation, and protoplast fusion. Liposomes may also be potentially beneficial for delivery of DNA into a cell.

Antisense-based strategies can be employed to explore MADR2 gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target MADR2 mRNA. Antisense strategies may use a variety of approaches including the use of antisense oligonucleotides, injection of antisense RNA and transfection of antisense RNA expression vectors. Antisense effects can be induced by control (sense) sequences; the extent of phenotypic changes, however, are highly variable. Phenotypic effects induced by antisense effects are based on changes in criteria such as protein levels, protein activity measurement, and target mRNA levels.

Transplantation of normal genes into the affected cells of a patient with a malignancy can also be useful therapy, especially if the malignancy is diffuse and cannot be excised or if the tissue affected has been substantially transformed into a malignant phenotype and due to its function in the body, cannot be surgically removed. In this procedure, normal MADR2 is transferred into a cultivatable cell type, either exogenously or endogenously to a patient. These cells are then injected serotologically into the targeted tissue(s).

Animal Models

The present invention also provides for the production of transgenic non-human animal models for the study of the MADR2 tumor suppressor gene function, to study the mechanisms of carcinogenesis as related to the MADR2 gene, for the screening of candidate pharmaceutical compounds, for the creation of explanted mammalian cell cultures which express the protein or mutant protein or in which the MADR2 gene has been inactivated by knock-out deletion, and for the evaluation of potential therapeutic interventions.

The creation of an animal model for colorectal cancer and other related cancers is important to the understanding of the MADR2 gene function in the cancer and for the testing of possible therapies. Although mutations in the MADR2 gene have to date only been found in sporadic colorectal tumours, it is understood that animal models are valuable to study the normal functioning of the gene in development and during tumorigenesis. This will permit the use of the animal as a model for cancer development in which different drugs, protein and gene therapies can be tested.

Animal species which are suitable for use in the animal models of the present invention include, but are not limited to, rats, mice, hamsters, guinea pigs, rabbits, dogs, cats, goats, sheep, pigs, and non-human primates such as monkeys and chimpanzees. For initial studies, transgenic mice and rats are highly desirable due to their relative ease of maintenance and shorter life spans. For certain studies, transgenic yeast or invertebrates may be suitable and preferred because they allow for rapid screening and provide for much easier handling. For longer term studies, non-human primates may be desired due to their similarity with humans.

There are several ways in which to create an animal model for mutated MADR2 leading to malignancy. Generation of a specific mutation in a homologous animal gene is one strategy. Secondly, a wild type human gene and/or a humanized animal gene could be inserted by homologous recombination. Thirdly, it is also possible to insert a mutant (single or multiple) human gene as genomic or minigene cDNA constructs using wild type or mutant or artificial promoter elements. Fourthly, knock-out of the endogenous homologous animal genes may be accomplished by the insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To inactivate the MADR2 gene chemical or x-ray mutagenesis of mouse gametes, followed by fertilization, can be applied. Heterozygous offspring can then be identified by Southern blotting to demonstrate loss of one allele by dosage, or failure to inherit one parental allele using RFLP markers.

To create a transgenic mouse, which is preferred, a mutant version of MADR2 can be inserted into a mouse germ line using standard techniques of oocyte microinjection or transfection or microinjection into embryonic stem cells. Alternatively, if it is desired to inactivate or replace the endogenous MADR2 gene, homologous recombination using embryonic stem cells may be applied.

For oocyte injection, one or more copies of the mutant or wild type MADR2 gene can be inserted into the pronucleus of a just-fertilized mouse oocyte. This oocyte is then reimplanted into a pseudo-pregnant foster mother. The liveborn mice can then be screened for integrants using analysis of tail DNA for the presence of human MADR2 gene sequences. The transgene can be either a complete genomic sequence injected as a YAC, BAC, PAC or other chromosome DNA fragment, a cDNA with either the natural promoter or a heterologous promoter, or a minigene containing all of the coding region and other elements found to be necessary for optimum expression.

Retroviral infection of early embryos can also be done to insert the mutant or wild type MADR2. In this method, the mutant or wild type MADR2 is inserted into a retroviral vector which is used to directly infect mouse embryos during the early stages of development to generate a chimera, some of which will lead to germline transmission. Similar experiments can be conducted in the cause of mutant proteins, using mutant murine or other animal MADR2 gene sequences. Although, to date, mutations in the MADR2 gene have not been found in the germ line, germ line transmission of both normal and mutant MADR2 gene sequences will be useful in the study of the mechanisms of tumour suppression function. It will also allow for testing of carcinogens to stimulate tumourigenesis in order to study tumourigenesis during development and elucidate effective treatments.

Homologous recombination using stem cells allows for the screening of gene transfer cells to identify the rare homologous recombination events. Once identified, these can be used to generate chimeras by injection of mouse blastocysts, and a proportion of the resulting mice will show germline transmission from the recombinant line. This methodology is especially useful if inactivation of the MADR2 gene is desired. For example, inactivation of the MADR2 gene can be done by designing a DNA fragment which contains sequences from a MADR2 exon flanking a selectable marker. Homologous recombination leads to the insertion of the marker sequences in the middle of an exon, inactivating the MADR2 gene. DNA analysis of individual clones can then be used to recognize the homologous recombination events.

It is also possible to create mutations in the mouse germline by injecting oligonucleotides containing the mutation of interest and screening the resulting cells by PCR.

In general, techniques of generating transgenic animals are widely accepted and practiced. A laboratory manual on the manipulation of the mouse embryo, for example, is available detailing standard laboratory techniques for the production of transgenic mice (Hogan et al., 1986).

This embodiment of the invention has the most significant potential as a model for colorectal cancer and related malignancies in which the function of the MADR2 gene could be studied as well as the effects of new therapeutic treatments and the design of new drug therapies. Animal models are also valuable in order to study the time frame in which an introduced mutation in the MADR2 gene causes a malignancy.

Drug Screening

Cell lines may be cultured which express MADR2, to which a test compound is added to the culture medium. After a period of incubation, the expression of MADR2 mRNA and resultant protein product can be quantified to determine any changes in expression as a result of the test compound. Cell lines transfected with constructs expressing mutant or normal MADR2 can also be used to test the function of compounds developed to modify with the protein function. Transformed cell lines expressing wild type MADR2 protein could be mutagenized by the use of mutagenizing agents to produce a malignant phenotype in which the role of mutated MADR2 can be studied.

With respect to normal MADR2, the effect of protein drugs/agents which interact with the proteins normal function could be studied in order to more precisely define the intracellular role of the protein. The phosphorylation of MADR2 by TGFβ stimulation leads to intracellular effects which directly or indirectly affect gene transcription. Therefore incubating cell cultures expressing MADR2 with agents that affect phosphorylation may help to elucidate the involvement of other proteins in transcription regulation. The addition of TGFβ or other TGFβ receptor agonists in the presence of [32p]-labelled medium agonists results in MADR2 phosphorylation and may lead to the identification of other proteins phosphorylated as a result of this stimulation. Agents such as phosphatases which stimulate protein dephosphorylation or drugs that modify phosphatase activity may also be used in order to study normal and mutant protein function. It is with the elucidation of the exact function of the protein and the components of the signalling pathway that it is involved which will allow for the development of novel drugs to restore normal function of the protein.

Since phosphorylation of MADR2 is required for its role in controlling normal cellular growth, it would be informative to study the lack or inhibition of phosphorylation in order to study the intracellular mechanisms involved in malignant transformation. The development of an in vitro assay for phosphorylation of MADR2 by the receptor complex allows for the design of drugs targeted to the receptor kinase that can specifically inhibit or abolish MADR2 phosphorylation or association of MADR2 with the receptors. The use of TGFβ binding, the oligomerization of the TGFβ complex and resulting MADR2 phosphorylation, are also informative in order to study the lack of intracellular signalling by MADR2 and the resulting malignant transformation.

Mutated MADR2, which is not phosphorylated in response to TGFβ stimulation, may associate with other proteins in a non-functional manner to alter gene transcription. Using cell culture systems, drugs may also be developed to disrupt such a negative association.

Analogous wild type MADR2 molecules could also be developed for therapy as well as pharmaceuticals to stimulate the binding of wild type MADR2 with TGFβ receptors in order to provide for normal intracellular signalling.

All testing for novel drug development is well suited to defined cell culture systems which can be manipulated to express normal or mutated MADR2 and study the result of TGFβ signalling and gene transcription. Animal models are also important for testing novel drugs. Antibodies generated to recognize mutant MADR2 and bind to novel drugs can be used to specifically target malignant tissues expressing mutant MADR2. In this manner only malignant cells can be targeted with potentially lethal pharmaceutical agents and not normal surrounding tissues.

EXAMPLES

The examples are described for the purposes of illustration and are not intended to limit the scope of the invention.

Methods of molecular genetics, protein and peptide biochemistry and immunology referred to but not explicitly described in this disclosure and examples are reported in the scientific literature and are well known to those skilled in the art.

Example 1

Identification of a MAD-Related Protein, MADR2

A database of expressed sequence tags (IMAGE; Lennon et al., 1996) was searched and two non-overlapping partial clones (Nos. 136422 and 145032) which contained open reading frames displaying similarity either to the amino or the carboxy terminus of MADR1were identified and sequenced using SEQUENASE™ 2.0 Kit (US Biochemicals). Both sequences contained 591 nucleotides, with 40 nucleotides upstream of the start codon ATG. A third clone with similarity to MADR1(No. 138604) appeared to contain a stop codon. To obtain the full-length coding sequence, primers encoding the predicted start and stop codons were designed for polymerase chain reaction and a human kidney cDNA library was used as template.

To obtain a full length cDNA, sense and antisense primers which contained convenient restriction sites for subcloning were designed based on the sequences obtained from the expressed sequence database clones. To allow introduction of an epitope tag into the amino terminus of the encoded protein, the start methionine in the sense primer was replaced with a SalI site and a glutamine residue to allow direct subcloning into pCMV5-Flag, a vector constructed by modifying pCMV5 to contain a Flag epitope tag with a SalI site at its 3' end (Hoodless et al., 1996). Polymerase chain reaction with a DNA isolated from a human kidney cDNA library (Clontech, pGAD424 library) was performed using a Perkin Elmer 9600 apparatus. To obtain the full cDNA coding sequence, multiple PCR-generated constructs were sequenced.

Example 2
Localisation of MADR2 to Chromosome 18q21
RH and YAC contig mapping

The following PCR primers specific for the 3'-UTR of MADR2 and DPC4 (MADR3) were designed using the Primer Version 3.0 program (Whitehead Institute/MIT Center for Genome Research): MADR2: forw. 5'-ACCAATCAAGTCCCATGAAA-3' (Sequence ID No: 21); rev. 5' TGATCGAGACCTCAAGTGCTG-3' (Sequence ID No: 22); DPC4.UTR: forw. 5'ATTGAAATTCACTTACACCGGG-3'(Sequence ID No: 23); rev. 5'-AGCCATGCCTGACAAGTTCT-3' (Sequence ID No: 24). The primers DCC.PCR2.1/2.2 and DCC.PCR36.1/36.2 which are specific for the most 5' and 3' exons, respectively, of DCC, are described in DGB. Information on all of the other primers shown in FIG. 1 is available from the MIT Genome Center. The conditions of PCR for all mapping experiments were: initial denaturation for 2 min at 94° C., followed by 36 cycles of denaturing for 40 sec at 94° C., annealing for 40 sec at 55° C. and extension for 40 sec at 72° C., 35 cycles. Radiation hybrid mapping experiments were carried out in duplicate using the Genebridge 4 panel (Walter et al., (1994); purchased from Research Genetics). The Whitehead Institute/MIT Center for Genome Research RH server was used to order the new STSs relative to framework markers. All of the protocols used for YAC manipulations have been described previously (Scherer and Tsui, 1991). MADR2 detected YACs C739a3, C749d11, C887e9, C929d7, C940e10, DPC4 was positive for C7474a6, C786c3, C917c8, C945b11, and C957b11, DCC.PCR2.1/2.2 detected 746h3, 787f7, 787g3, 818e6, 821b7, 838b4, 849d6, 945b11, and 956a9, and DCC.PCR36.1/36.2 identified 782g1, 787f7, 790d12, 821b7, 830g12, 838b4, 905e8, 945b11, and 966e5.

Regional Localisation of MADR2 to chromosome 18q21 near DPC4 and DCC.

The chromosomal localisation of MADR2 was determined using a combination of radiation hybrid (RH) mapping, yeast artificial chromosome (YAC) contig analysis, and fluorescence in situ hybridization (FISH). PCR primers designed from the 3'-UTR of MADR2 were initially used to screen the GeneBridge 4 RH panel (Walter et al., 1994) and the results indicates the gene residues on chromosome 18q21 approximately 9.3 cR from D18S460. The same primers were also used to screen the CEPH mega YAC library (Chumakov et al., 1995) and 5 YACs (739a3, 749d11, 887e9, 929d7, 940e10) were identified. These clones were shown previously by the Whitehead Institute/MIT Center for Genome Research to map within a well-defined YAC contig on chromosome 18 (named WC18.5). This contig encompasses the same DNA marker, D18S460, that was linked to MADR2 on the RH map (Hudson et al., 1996) and further analysis of the YACs identified 3 clones that contained both MADR2 and D18S460 (FIG. 1). The cytogenetic position of MADR2 was confirmed further by FISH mapping two gene-specific P1-derived artificial chromosome clones (PACs 66i18 and 201n19) to 18q21 (data not shown).

MADR2 mapped to chromosome 18q21 and this prompted the determination of its relative location with respect to DPC4 and DCC, which also map to 18q21 (Hahn et al., 1996a) and have been shown to be frequently deleted in pancreatic cancer (Hahn et al. 1996a; Hahn et al., 1996b) and colon cancer (Fearon et al., 1990; Vogelstein et al., 1988), respectively. Accordingly, gene-specific sequence-tagged sites (STSs) for DPC4 and DCC were tested against the RH panel and all of the YAC clones from the Wc18.5 contig. Using the previously published YAC and RH map (Hudson et al., 1996) as a framework, the following order was established; 18cen-MADR2-DPC4-DCC-18qter (FIG. 1). Both the YAC and RH data for the genes were in complete agreement.

The STS content data of the YACs suggested the orientation of DCC, which spans approximately 1.3 Mb of DNA (Cho et al., 1994), along the chromosome to be 18cen-5'-DCC-3'-18qter. MADR2 was shown to map to 18q21, DPC4 mapped to 18q21.1 (Hahn et al., 1996a), and DCC mapped to 18q21.3 (GDB).

Example 3
Phosphorylation of MADR2 by TGFβ Signalling Pathways

To examine which ser/thr kinase receptor activated pathways regulate MADR2, constitutively active type I ser/thr kinase receptors were used. These type I receptors, generated by the introduction of a charged residue in the highly conserved GS domain (Attisano et al., 1996; Hoodless et al., 1996; Wieser et al., 1995), signal in the absence of ligand and type II receptors (Wieser et al., 1995). To facilitate the analysis, a mammalian expression vector was constructed which encodes a Flag epitope tag at the amino terminus of MADR2 (Flag/MADR2).

For the generation of stable transfectants, Flag/MADR2 was subcloned into pMEP4 (Invitrogen) behind a metallothionein inducible promoter using convenient sites in the vector polylinker regions (Wrana et al., 1994). To generate Flag/MADR2 harbouring mutations, a fragment of MADR2 from an internal BglII site to the stop codon, which includes the site of mutation, was amplified by PCR using cDNA prepared from colorectal carcinoma RNA samples as template. The amplified region was subcloned into the full length Flag/MADR2 in pCMV5 and the presence of the missense mutations confirmed by sequencing of the amplified region.

Cell Lines and Transfections

COS-1 cells were grown in Dulbecco's minimal essential media containing high glucose and 10% fetal calf serum. Cells were transfected using the DEAE-dextran procedures as described previously (Hoodless et al., 1996). The Mv1Lu mink lung cell line (CCL-64) was maintained in minimal essential medium supplemented with 10% fetal bovine serum and non-essential amino acids (Gibco/BRL). Cells expressing Flag/MADR2 in pMEP4 (Invitrogen) were generated by transfection with lipofection (Gibco/BRL) as described previously (Wrana et al, 1992). To select for table transfectants, cells grown for 2 days were subcultured into two 150 mm dishes and grown in the presence of 300 μg/ml of hygromycin B (400U/mg; Calbiochem) for 2–3 weeks with a media change every 3–4 days. Pools of cell colonies were prepared by trypsinization of each 150 mm dish and cell stocks were maintained in the continuous presence of hygromycin. FlagMADR2 expression was induced by the overnight incubation of cells in medium containing 0.2% serum and 50 μM $ZnCl_2$.

Immunoprecipitation and Immunoblotting

Stably or transiently transfected cells were labelled for 2 hours with [$^{32}$P]phosphate as described previously (Attisano et al., 1996; Wrana et al., 1994). For stable cell lines, $Zn^{2+}$ induced monolayers were incubated in the presence or absence of 100 pM TGFβ (R & D Systems) in the last 15 min of the phosphate-labelling. Cell lysates were subjected to immunoprecipitation with anti-FLAG M2 monoclonal antibody (IBI, Eastman Kodak) followed by adsorption to protein G-SEPHAROSE (Pharmacia). Immunoprecipitates were washed, separated by SDS-PAGE and visualised by autoradiography. For determination of MADR2 protein levels, lysates were prepared from cells treated in parallel with those subjected to in vivo phosphate labelling. Proteins from cell lysates were separated by SDS-PAGE and transferred to nitrocellulose membranes. Flag/MADR1 was detected using anti-FLAG M2 antibody (1:3000 dilution) and chemiluminesence as recommended by the manufacturer (ECL Kit, Amersham).

To determine whether MADR2 is a target of TGFβ or BMP signalling pathways, COS cells were transiently transfected with FlagMADR2 alone or together with wild type or activated TβRI or ALK-3 (a BMP type I receptor). Flag-MADR2 was isolated by immunoprecipitation from [$^{32}$P] phosphate-labelled transfectants. Analysis of the immunoprecipitates revealed that phosphorylation of MADR2 was unaffected by the coexpression of wild type TβR-I, wild type ALK-3 or activated ALK-3 (FIG. 2). MADR2 phosphorylation was substantially increased in cells cotransfected with activated TβRI. Immunoblotting with anti-fla antibody of total cell lysates prepared in parallel confirmed that approximately equivalent amounts of MADR2 protein were examined (FIG. 2). In a parallel analysis of MADR1, increased phosphorylation was detected only in cells cotransfected with constitutively active ALK-3 as shown previously (data not shown; Hoodless et al., 1996).

Mv1Lu epithelial cell lines were stably transfected with FlagMADR2 under the control of an inducible metallothionein promoter in order to determine whether MADR2 phosphorylation was regulated in a TGFβ-dependent manner, (Wrana et al., 1992). Two independent pools of cells expressing Flag MADR2 in a zinc-inducible manner were generated and the regulation of MADR2 phosphorylation in response to TGFβ was examined. Analysis of MADR2 immunoprecipitated from [$^{32}$P]phosphate-labelled cells that were untreated or treated with TGFβ for 15 min revealed a ligand-dependent phosphorylation in both pools (FIG. 2). Thus, brief treatment of epithelial cells with TGFβ induces phosphorylation of MADR2.

Example 4
Detection of MADR2 Mutations in Colorectal Carcinoma
Mutational Analysis cDNA was synthesised from tissue total RNA using MMLV reverse transcriptase (Gibco-BRL) and random hexamers (Boehringer Mannheim). Each SSCP PCR reaction was carried out in a 20 μl reaction composed of 1×PCR buffer (10 mM Tris-HCl pH 8.3, 50 mM KCl, 0.01% gelatin), 1.6 mM MgCl2, 30 uM each dNTPs, 9 pmole of each forward and reverse primer, cDNA made from 25 ng of RNA, 1.5 uCi [$^{33}$P]-dATP (2000 Ci/mmol, Nen-DuPont) and 1 unit AMPLITAQ DNA polymerase (Perkin-Elmer). Region 1 (nucleotide 279 to 542), 2 (nucleotide 778 to 1014), 3 (nucleotide 1182 to 1430), and 4 (nucleotide 953 to 1245) were amplified with the following primers: Region 1: 5'-AGATCAGTGGGATACAACAGG-3' Sequence ID No: 5 and 5'-GGCACTAATCTGGAGGCAA-3' Sequence ID No: 6 (265 bp); Region 2: 5'-AGCTTGGATTTACAGCCAGT-3' Sequence ID No: 7 and 5'-TAAGCTCACTCCTCTTCCTA-3' Sequence ID No: 8 (237 bp); Region 3: 5'-GGCTCAGTCTGTTAATCAGG-3' Sequence ID No: 9 and 5'-TTCCATGGGACTTGATTGGTT-3' Sequence ID No: 10 (249 bp); Region 4: 5'-TGTTAACCGAAATGCCACGG-3' Sequence ID No: 11 and 5'-TCTTATGGTGCACATTCTAGT-3' Sequence ID No: 12 (293 bp). Regions 1 and 2 were amplified simultaneously in the same reaction tube. Cycling conditions involved 35 cycles of 94° C. 15 seconds, 55° C. 15 second and 72° C. for 20 second using the 9600 THERMCYCLER (Perkin-Elmer). PCR product were mixed with 2 volumes of denaturing dye (95% formamide, 20 mM EDTA, 0.05% Bromophenol Blue and 0.05% Xylene Cyanol FF), heat denatured and loaded on a SSCP gel (8% acrylamide:bis-acrylamide (40:1), 0.5×TBE and 10% glycerol). Electrophoresis was carried out at 16° C. using a STRATATHERM Cold temperature controlled apparatus (Strategene). Mutations were confirmed by direct sequencing of asymmetric PCR product using the Sequenase v2.0 kit (USB).

MADR2 is Mutated in Colorectal Carcinoma

A variety of human tumours were examined for mutations in MADR2 using single strand conformation polymorphism (SSCP) analysis of CDNA. The examination focussed on the MH1 and MH2 domains of MADR2 which display the highest degree of similarity amongst members of the MAD family. Furthermore, it is within the MH2 domain that all of the identified mutations in DPC4 reside (Hahn et al., 1996a). An initial screen of 101 axillary node-negative breast carcinomas and 76 sarcomas (which included 35 osteosarcomas) did not reveal any mutations, with the exception of a benign polymorphism (R415R) in one breast cancer sample. In a screen of 66 sporadic solon carcinomas, four missense mutations (6%) were identified. Three of these mutations altered highly conserved residues within the MH2 domain and involved two non-conservative (P445H and L440R) and one conservative (D450E) amino acid change (FIG. 3 and Table 3). The fourth missense mutation mapped to the MH1 domain and resulted in the alteration of a highly conserved arginine residue to a cysteine (R133C; FIG. 3 and Table 3). In the three cases where normal tissue was available (213, 357 and 348), MADR2 was found to have wild-type sequence, indicating that these mutations were acquired as somatic events. SSCP band intensities were also analysed. Comparison of mutant and wild type alleles in each tumour sample showed that tumours 357 and 369 had little or no wild type message, suggesting LOH at this locus.

The regulation of the mutant proteins by the TGFβ signalling pathway was examined. To test this, the mutations L440R, P445H and D450E were introduced into wild type Flag/MADR2 as follows.

A fragment of MADR2, from an internal BglII site to the stop codon which includes the site of mutation, was amplified by polymerase chain reaction using cDNA prepared from colorectal carcinoma RNA samples as template. The amplified region was subcloned into the full length Flag/MADR2 in pCMV5 and the presence of the missense mutations confirmed by sequencing of the amplified region.

The protein was expressed in COS-1 cells together with either wild type or constitutively active TβRI. Relative phosphorylation levels were assessed by immunoprecipitation of MADR2 protein from [$^{32}$P]phosphate-labelled cells and quantifying protein levels by western-blotting of whole cell lysates. When wild type MADR2 was coexpressed with activated TβR-I, typical elevations in phosphorylation of MADR2 were observed (FIG. 4). In contrast, two of the MADR2 mutants 213 and 357 (P445H and D450E, respectively), showed no alternations in relative phosphorylation upon coexpression with activated receptors. Thus, both the nonconservative P445H and the conservative D450E mutations disrupt the regulation of MADR2 phosphorylation.

Example 5
Induction of Morphogenetic Movements and Mesoderm by Wild-Type but not Mutant MADR2 Proteins Animal caps cut from embryos injected with wild-type MADR2 caps elongated as they underwent morphogenetic movements associated with mesoderm differentiation. Control caps and caps expressing mutant MADR2 proteins did not. Intact embryos expressing mutant and wild-type MADR2 in the animal pole were also scored for extopic sites of gastrulation. The control embryo was indistinguishable from embryos that expressed the mutant forms of MADR2 (FIG. 5A). An embryo expressing wild-type MADR2 showed an additional invagination furrow (white arrow) whose time of appearance coincided with the formation of the dorsal lip of the Spemann organizer, the normal site of gastrulation initiation. The normal gastrulation furrow (black arrow) of the embryo pictured in FIG. 5A is displaced from its usual, more vegetal, position because of the action of the ectopic furrow. All wild-type MADR2-injected embryos displayed the phenotype shown (for all sets of embryos n>12). The embryos analyzed were siblings of those used in the animal cap assays in B, all of which expressed MADR2 proteins.

For RT-PCR analysis, animal caps were injected with wild-type and mutated MADR2 mRNAs and showed that only wild type, and not mutated, MADR2 induces mesoderm as scored by the expression of brachyury, a general mesoderm marker at early to mid-gastrulation (FIG. 5B). Caps were injected with control (C;pGEM vector transcripts) and wild-type or mutant MADR2 mRNAs as indicated. EF1-α expression was scored as a general marker for RNA recovery. The emb RT + and − lanes are positive and negative controls using total embryonic RNA that was (+) or was not (−) reverse transcribed. A western blot of animal cap proteins stained with an anti FLAG antibody is shown in the lower panel. The western confirms that the various MADR2 proteins were synthesized in each set of caps, although mutant 369 displayed a lower level of expression. Ten animal caps were pooled for each sample analyzed by western blot and two cap equivalents were loaded per lane. Approximately 24 caps were cut at late blastula (stage 8), and at mid-gastrula (stage 12) half were harvested for RT-PCR and half for protein analysis.

For the Xenopus embryonic assays, the cDNAs for MADR2 and its mutant forms were subcloned into the CS2+ vector (Rupp et al., 1994), and plasmids were linearized with Not1 prior to SP6 transcription of capped synthetic mRNA (using the mMESSAGE MACHINE kit, Ambion Inc.). Transcripts from a linearized vector (pGEM7) served as a negative control for mRNA injection. 1.0 ng of each mRNA was injected into the animal pole of a two-cell blastula (0.5ng per blastomere) and animal caps were excised at blastula stage 8 and cultured in vitro, or the embryos were allowed to develop intact to assay ectopic gastrulation movements. Proteins for western blots were prepared by lysing animal caps (10 caps per 100 μl) directly in 2× Laemmli gel loading buffer. RNA was prepared from animal caps and RT-PCR performed as described (Thomsen 1996, Wilson et al., 1994) using a 25 μl reaction volume. One half of a cap or 0.2 embryo equivalents were analyzed by RT-PCR, using 17 cycles of amplification for Efl-α and 24 cycles for Xbra. One fifth of each sample was loaded on a 6% PAGE (0.5× TBE) gel. Film (KODAK XAR) was exposed for three hours to detect Efl-α and the embryo RT+ and − lanes of Xbra. Xbra signals from animal caps were exposed for six hours.

Example 6
The Interaction of MADR2 with TGFβ receptors.

COS-1 cells transiently transfected with empty vector (−) or FlagMADR2 and the indicated combinations of wild type (WT) or kinase deficient (KR) TβRI and HA-tagged TβRII were affinity labelled with [$^{125}$I]TGFβ. Cell lysates were subjected to immunoprecipitation with anti-Flag M2 antibody (α-Flag IP) and receptor complexes visualized by SDS-PAGE and autoradiography (FIG. 6A). To confirm equivalent levels of receptor expression aliquots of the total cell lysates were analyzed by SDS-PAGE (bottom panel of FIG. 6A, receptors).

To determine whether MADR2 function requires interaction with activated TβRI receptor, COS-1 cells were transfected with FlagMADR2 and the indicated receptor constructs, were processed as described above. Equivalent expression of FlagMADR2 protein was determined by immunoblotting total cell lysates using anti-Flag M2 antibodies (bottom panel of FIG. 6B, α-Flag blot).

For transfection, COS-1 cells were transfected with DEAE-dextran were affinity-labelled using 200 pM [$^{125}$I] TGFβ and the receptors were cross-linked to the ligand as described previously (Massagué 1987). Cells were lysed in lysis buffer as described by Wrana et al., 1994, containing 10% glycerol. For determining MADR2 receptor complex interactions, lysates were immunoprecipitated using an anti-Flag M2 monoclonal antibody (IBI, Eastman Kodak) as described in Hoodless et al., 1996. For immunoblotting, aliquots of total cell lysates were separated by SDS-PAGE, transferred to nitrocellulose and protein detected using anti-Flag M2 antibody and chemiluminescence (ECL, Amersham).

Example 7
Phosphorylation of MADR2 in Vitro by Isolated Receptor Complexes

Non-transfected Mv1Lu cells or L17 cells transiently transfected with empty vector (pCMV5) or both TβRI and HA-tagged TβRII were incubated with (+) or without (−) TGFβ (0.5 nM) for 30 minutes at 37° C. Receptor complexes were isolated by immunoprecipitation using α-HA or α-TβRII antibodies as indicated and then were incubated in kinase assay buffer containing [γ$^{32}$P]ATP and bacterially expressed MADR2 fusion protein (GST-MADR2) as substrate. The results of this phosphorylation is shown in FIG. 7A.

For in vivo phosphorylation of MADR2, COS-1 cells were transfected with FlagMADR2 and either wild type (TβRI) or constutively active (*TβRI) TβRI were labelled with [$^{32}$P]phosphate and MADR2 was purified by immunoprecipitation with anti-M2 Flag antibodies as shown in FIG. 7B.

For in vitro phosphorylation of MADR2, COS-1 cells were transfected with TβRII and TβRI were incubated for 15 minutes with TGFβ and isolated receptors were subjected to an in vitro kinase assay as described above. These results are shown in FIG. 7C.

For the tryptic phosphopeptide mapping of in vivo and in vitro labelled MADR2, tryptic digests of gel-purified MADR2, from the indicated lanes in FIGS. 7A, 7B and 7C, were resolved in two dimensions with electrophoresis in pH 1.9 buffer and chromatography in phosphochromatography buffer as described previously (Wrana et al., 1994, Boyle et al., 1991). The relevant phosphopeptides (arrows) and the location of the sample application (+) are indicated. Mix, mixture of aliquots from b, lane *TβRI and from c, lane RII+RI.

For the transfections, L17 and COS-1 cells were transiently transfected using the DEAE-Dextran method (Hoodless et al., 1996). For the in vitro kinase assays, cells were lysed in lysis buffer as done in example 5. The receptor complex was immunoprecipitated with an anti-TβRII antibody (C16, Santa Cruz) or anti-HA monoclonal antibody (12CA5). The isolated receptor complex was incubated in kinase buffer (5 mM Tris, pH 7.4, 1 mM $MgCl_2$, 0.1 mM $CaCl_2$) containing 1 μM ATP, 20 μCi[$\gamma^{32}$P]ATP and MADR2 protein which was expressed in bacteria as a Glutathione-S-Transferase (GST) fusion protein. MADR2 phosphorylation was analyzed by SDS-PAGE and autoradiography.

Example 8
Phosphorylation of MADR2 In Vitro by Wild Type and Kinase Deficient Receptor Complexes Phosphorylation of MADR2 in vitro by wild type and kinase deficient receptor complexes is shown in FIG. 8A. COS-1 cells were transiently transfected with empty vector (−) or with combinations of wild type (WT) and kinase deficient (KR) forms of TβRI and HA-tagged TβRII. Cells were incubated with TGFβ for 15 minutes at 37° C., lysed and receptor complexes were incubated in kinase assay buffer containing [$\gamma^{32}$P]ATP and bacterially expressed MADR2 fusion protein (GST-MADR2) as substrate. MADR2 phosphorylation was visualized by SDS-PAGE and autoradiography. The coomassie stained gel indicating constant levels of MADR2 protein is shown (middle panel). To confirm that equivalent amounts of receptor complex were present in the kinase assays, aliquots of transfected cells plated in parallel were affinity-labelled with [$^{125}$I]TGFβ as in FIG. 6 and receptors were immunoprecipitated with anti-HA antibody (bottom panel, receptors). The migration of TβRII and TβRI is indicated.

Phosphotide mapping of tryptic digests of gel-purified MADR2 is shown in FIG. 8B and was done by resolving the digests in two dimensions and visualizing by autoradiography. The relevant phosphopeptides (arrows) and the location of the sample application (+) are indicated. The in vitro kinase assays, affinity-labelling and phosphopeptide mapping were performed as described in Examples 6 and 7.

Example 9
Specificity of Receptor Association

COS-1 cells were transfected with FlagMADR2 or FlagDPC4 together with TβRII and either wild type (WT) or kinase deficient (KR). TβRI were affinity-labelled with [$^{125}$I]TGFβ. FlagMADR2 and FlagDPC4 were immunoprecipitated with anti-Flag M2 antibodies and associated receptors visualized by SDS-PAGE and autoradiography (shown in FIG. 9A). To confirm constant receptor expression levels, aliquots of total cell lysates were similarly examined (receptors, middle panel). Equivalent expression of Flag-MADR2 protein was determined by immunoblotting total cell lysates using anti-M2 antibody (bottom panel, α-Flag blot).

Figure 9C:
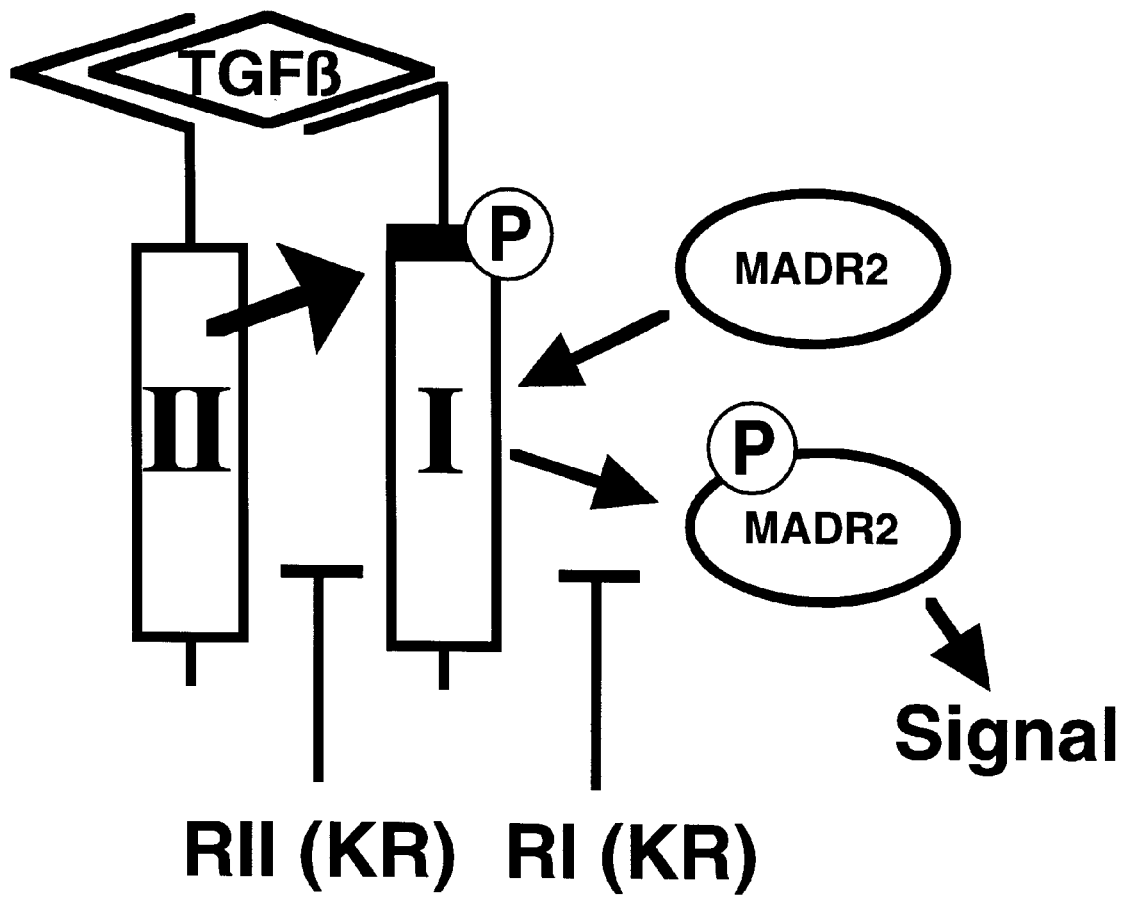
FIG. 9C shows a diagram of a model for intracellular signalling by MADR2 in the TGFβ pathway.

FIG. 9B shows the analysis of phosphorylation of MADR2 and DPC4 in vitro. COS-1 cells were transiently transfected with empty vector (−) or with TβRI and HA-tagged TβRII and were incubated with TGFβ for 30 minutes at 37° C. Cells were lysed and receptor complexes isolated by immunoprecipitation using anti-HA antibodies. Receptor complexes were subjected to an in vitro kinase assay with bacterially expressed MADR2 or DPC4 as indicated (substrate). Phosphorylation of MADR2 and DPC4 was visualized by SDS-PAGE and autoradiography (shown in FIG. 9B). The coomassie stained gel indicating the relative level of MAD-related proteins is shown (middle panel).

The affinity-labelling, in vitro kinase assays and immunoblotting were performed as described for examples 5 and 6. The mouse DPC4 was isolated by low stringency screening of a mouse 16 day embryo library (Novagen). For expression in mammalian cells and in bacteria, a full length clone was subcloned into pCMV5-Flag as described for MADR1(Hoodless et al., 1996) or in pGEX4T1, respectively.

The present invention is not limited to the features of the embodiments described herein, but includes all variations and modifications within the scope of the claims.

TABLE 1

(Sequence ID No:1)
TTTTCCTAGCGTGGCTTGCTGCCTTTGGTNAAGAACATGTCGTCCAT

CTTGCCATTCACGCCGCCAGTTGTGAAGAGACTGCTGGGATGGAAGAA

GTCAGCTGGTGGGTCTGGAGGAGCAGGCGGAGGAGAGCAGAATGGGCA

GGAAGAAAAGTGGTGTGAGAAAGCAGTGAAAAGTCTGGTGAAGAAGCT

AAAGAAAACAGGACGATTAGATGAGCTTGAGAAAGCCATCACCACTCA

AAACTGTAATACTAAATGTGTTACCATACCAAGCACTTGCTCTGAAAT

TTGGGGACTGAGTACACCAAATACGATAGATCAGTGGGATACAACAGG

CCTTTACAGCTTCTCTGAACAAACCAGGTCTCTTGATGGTCGTCTCCA

GGTATCCCATCGAAAAGGATTGCCACATGTTATATATTGCCGATTATG

GCGCTGGCCTGATCTTCACAGTCATCATCAACTCAAGGCAATTGAAAA

CTGCGAATATGCTTTTAATCTTAAAAAGGATGAAGTATGTGTAAACCC

TTACCACTATCAGAGAGTTGAGACACCAGTTTTGCCTCCAGTATTAGT

GCCCCGACACACCGAGATCCTAACAGAACTTCCGCCTCTGGATGACTA

TACTCACTCCATTCCAGAAAACACTAACTTCCCAGCAGGAATTGAGCC

ACAGAGTAATTATATTCCAGAAACGCCACCTCCTGGATATATCAGTGA

AGATGGAGAAACAAGTGACCAACAGTTGAATCAAAGTATGGACACAGG

CTCTCCAGCAGAACTATCTCCTACTACTCTTTCCCCTGTTAATCATAG

CTTGGATTTACAGCCAGTTACTTACTCAGAACCTGCATTTTGGTGTTC

GATAGCATATTATGAATTAAATCAGAGGGTTGGAGAAACCTTCCATGC

ATCACAGCCCTCACTCACTGTAGATGGCTTTACAGACCCATCAAATTC

AGAGAGGTTCTGCTTAGGTTTACTCTCCAATGTTAACCGAAATGCCAC

TABLE 1-continued

GGTAGAAATGACAAGAAGGCATATAGGAAGAGGAGTGCGCTTATACTA
CATAGGTGGGGAAGTTTTTGCTGAGTGCCTAAGTGATAGTGCAATCTT
TGTGCAGAGCCCCAATTGTAATCAGAGATATGGCTGGCACCCTGCAAC
AGTGTGTAAAATTCCACCAGGCTGTAATCTGAAGATCTTCAACAACCA
GGAATTTGCTGCTCTTCTGGCTCAGTCTGTTAATCAGGGTTTTGAAGC
CGTCTATCAGCTAACTAGAATGTGCACCATAAGAATGAGTTTTGTGAA
AGGGTGGGGAGCAGAATACCGAAGGCAGACGGTAACAAGTACTCCTTG
CTGGATTGAACTTCATCTGAATGGACCTCTACAGTGGTTGGACAAAGT
ATTAACTCAGATGGGATCCCCTTCAGTGCGTTGCTCAAGCATGTCATA
AAGCTTCACCAATCAAGTCCCATGGAAAAGACTTAATGTAACAACTCT
TCTGTTCATTAGCATTGTGTTGTNGTCCCTATGGGACTGTTTACTATT
CCAAAAGTTTCAAGGAGAGAAAACAGCANTTGAGGTCTCCNTCATTTA
AAGNACCCTGTNGGATTTTTTTT

TABLE 2

(Sequence ID NO:2)
MSSILPFTPPVVKRLLGWKKSAGGSGGAGGGEQNGQEEKWCEKAVKSL
VKKLKKTGRLDELEKAITTQNCNTKCVTIPSTCSEIWGLSTPNTIDQW
DTTGLYSFSEQTRSLDGRLWVSHRKGLPHVIYCRLWRWPDLHSHHELK
AIENCEYAFNLKKDEVCVNPYHYQRVETPVLPPVLVPRHTEILTELPP
LDDYTHSIPENTNFPAGIEPQSNYIPETPPPGYISEDGETSDQQLNQS
MDTGSPAELSPTTLSPVNHSLDLQPVTYSEPAFWCSIAYYELNQRVGE
TFHASQPSLTVDGFTDPSNSERFCLGLLSNVNRNATVEMTRRHIGRGV
RLYYIGGEVFAECLSDSAIFVQSPNCNQRYGWHPATVCKIPPGCNLKI
FNNQEFAALLAQSVNQGFEAVYQLTRMCTIRMSFVKGWGAEYRRQTVT
STPCWIELHLNGPLQWLDKVLTQMGSPSVRCSSMS

TABLE 3

Amino Acid Sequence of MADR2 (Sequence ID No:2)

```
                                 50
      |─────────────── MH1 ──────────────────────────|
MSSILPFTPPVVKRLLGWKKSAGGSGGAGGGEQNGQEEKWCEKAVKSLVKKLKKTGRLDELEKAITTQNCNTKCVTIP 78

STCSEIWGLSTPNTIDQWDTTGLYSFSEQTRSLDGRLQVSHRKGLPHVIYCRLWRWPDLHSHHELKAIENCEYAFNLK 156
                                                  ↓
                                                55 C
KDEVCVNPYHYQRVETPVLPPVLVPRHTEILTELPPLDDYTHSIPENTNFPAGIEPQSNYIPETPPPGYISEDGETSD 234

|─────────────────────────────────────────
QQLNQSMDTGSPAELSPTTLSPVNHSLDLQPVTYSEPAFWCSIAYYELNQRVGETFHASQPSLTVDGFTDPSNSERFC 312
                              ─────────────── MH2 ────────────────
LGLLSNVNRNATVEMTRRHIGRGVRLYYIGGEVFAECLSDSAIFVQSPNCNQRYGWHPATVCKIPPGCNLKIFNNQEF 390
                             60
────────────────────────────────────────────────────────────────────────────|
AALLAQSVNQGFEAVYQLTRMCTIRMSFVKGWGAEYRRQTVTSTPCWIELHLNGPLQWLDKVLTQMGSPSVRCSSMS 467
                           ↓     ↓   ↓
                           R     H   E
```

The highly conserved MH1 (solid overline) and MH2 (dashed overline) are indicated. The missense mutations identified in colorectal carcinoma samples are shown (arrows). Amino acid residues are numbered at the right.

TABLE 4

Sequence comparison of mammalian MAD-related proteins

```
                                                                                                                                                      MH1
MADR2 (Sequence ID No:13)    M..sSILPF.TPPV.....VKRLLGWKKSAGGSGAGGEQNGQEEKWCEKAVKSLVKKLKKT.GRLDELEKAIT                     66
MADR1 (Sequence ID No:2)     M.NVTSLFSF.TSPA....VKRLLGWKQ...........GDEEKWAEKAVDALVKKLKKKGAMEELEKALS                      56
DPC4  (Sequence ID No:14)    M.DNMSITNTPTSNDACLSIVHSLMCHRQ..........GGESETFAKRAIESLVKKLKEKKDELDSLITAIT                    62

TQNC.NTKCVTIPSTCSEIWGLSTPNTIDQWDTTGLYSFSEQTRSLDGRLQVSHRKGLPHVIYCRLWRPDLHSHH                  141
MADR2                        CPGQ.PSNCVTIP.............................RSLDGRLQVSHRKGLPHVIYCRVWRPDLQSHH                  101
MADR1                        TNGAHPSKCVTIQ.............................RTLDGRLQVAGRKGFPHVIYARLWRPDL.HKN                  107
DPC4

ELKAIENCEYARNLKKDEVCVNPYHYQRVETPVLPPVLVPRHTEI....LTELPLDDYTHSIPENTNFPAGIE                    211
MADR2                        ELKPLECCEFPRGSKQKEVCINPYHYKRVESPVLPPVLVPRHSEYNPQHSLLAQFRNLGQNEPHMPLNATFPDSFQ                  177
MADR1                        ELKHVKYCQYARDLKCDSVCVNPYHYERVVSPGIDLSGLTLQSNAPSSMMVKDEYVHDFEGQPSLSTEGHSIQTIQ                  183
DPC4

.....PQSNYIPE..............................TPPPGYIS.EDGETSDQQLNQSMDTGSPAELS                  250
MADR2                        QPNSHPFPHSPNSISYPNSPGSSSSSTYPHSPTSSDPGSPFQMPADTPPPAYLPPEDPMTQDGS..QPMDTNMMAPPL                251
MADR1                        HPPSNRASTETYSTPALLAPSESNATSTANFPNIPVASTSQPASILGGSHSEGLLQIASGPQPGQQQNGFTGQPAT                 259
DPC4

PTTLSPVNHSLDLQP...........................VTYSEPAFWCSTAYYELNQRV                             286
MADR2                        P..SEINRG.DVQA.............................VAYEEPKHWCSIVYYELNNRV                            283
MADR1                        YHHNSTTTWTGSRTAPYTPNLPHHQNGHLQHHPPHPGHYWPVHNELAFQPPISNHPAPEYWCSIAYFEMDVQV                    335
DPC4                                                                                        MH2

GETFHASQPS...LTVDGFTDPSNSE.RFCLGLLSNVNRNATVEMTRRHIGRGVRLYYIG.GEVFAECLSDSAIFVQ                 358
MADR2                        GEAFHASSTS..VLVDGFTDPSNKNRRFCLGLLLSNVNRNSTIENTRRHIGKGVHLYYVG.GEVYAECLSDSSIFVQ                 356
MADR1                        GETFKVPSSCPIVTVDGYVDPSGGD.RFCLGQLSNVHRTEAIEARLHIGKGVQLECKGEGDVWVRCLSDHAVFVQ                  410
DPC4

SPNCNQRYGWHPAT.VCKI.PPGCNLKIFNN.QEFAALLAQ..................SV                               398
MADR2                        SRNCNYHHGFHPTT.VCKI.PSGCSLKIFNN.QEFAQLLAQ..................SV                               396
MADR1                        SYYLDREAGRAPGDAVHKIYPSAY.IKVEDLRQCHRQMQQQAATAQAAAAAQAAAVAGNIPGPGSVGGIAPAISLS                 485
DPC4

NQGFEAVYQLTRMCTIRMSFVKGWGAEYRRQTVTSTPCWIELHLNGPLQWLDKVLTQMGSPSVRCSSMS*                       467
MADR2                        NHGFETVYELTKMCTIRMSFVKGWGAEYHRQDVTSTPCWIELHLHGPLQWLDKVLTQMGSPHNPISSVS*                       465
MADR1                        AAAGIGVDDLRRLCILRMSFVKGWGPDYPRQSIKETPCWIEIHLHRALQLLDEVLHTM..PIADPQPLD*                      552
DPC4
```

Alignment of the predicted amino acid sequences of human MADR1, MADR2 and DPC4. Residues conserved in all three sequences are boxed and the MH1 and MH2 regions at the amino acid and carboxy termini are indicated (MH1, solid overline; MH2, dashed overline); Gaps introduced to maximize alignment are shown as dots and the amino acid residues are numbered on the right.

TABLE 5

| Sample | Codon | Mutation | Amino Acid Change | Normal tissue | Effect |
|---|---|---|---|---|---|
| 213 | 445 | CCT to CAT | Pro to His | wild type | no phosphorylation |
| 369 | 440 | CTT to CGT | Leu to Arg | wild type | unstable protein |
| 357 | 450 | GAC to GAG | Asp to Glu | N/A | no phosphorylation |
| 348 | 133 | CGC to TGC | Arg to Cys | wild type | not done |

TABLE 6

(Sequence ID NO:3)
AGGAACAAAAGGTCCGGGGCCCGGCTCGGACCCGGGGACCAGGCGCTG

GGTGCAGGGTAGATTTACCGGGCTTTTTCTGAGTGTGGATTGTTACCT

TTGGTAAGAAAATGTCGTCCATCTTGCCATTCACTCCGCCAGTGGTGA

AGAGACTTCTGGGATGGAAAAAATCAGCCGGTGGGTCTGGAGGAGCAG

GTGGTGGAGAGCAGAATGGACAGGAAGAAAAGTGGTGTGAAAAAGCAG

TGAAAAGTCTGGTGAAAAAGCTAAAGAAAACAGGACGGTTAGATGAGC

TTGAGAAAGCCATCACCACTCAGAATTGCAATACTAAATGTGTCACCA

TACCAAGCACTTGCTCTGAAATTTGGGGACTGAGTACAGCAAATACGG

TAGATCAGTGGGACATAACAGGCCTTTACAGCTTCTCTGAACAAACCA

GGTCTCTTGATGGCCGTCTTCAGGTTTCACACCGGAAAGGGTTGCCAC

ATGTTATATATTGCCGGCTCTGGCGCTGGCCGGACCTTCACAGTCATC

ATGAGCTCAAGGCAATCGAAAACTGCGAATATGCTTTTAATCTGAAAA

AAGATGAAGTGTGTGTAAATCCGTACCACTACCAGAGAGTTGAGACCC

CAGTCTTGCCTCCAGTCTTAGTGCCTCGGCCAACGGAGATTCTAACAG

AACTGCCGCCCTGGATGACTACACCCACTCCATTCCAGAAAACACAA

ATTTCCCAGCAGGAATTGAGCCACAGAGTAATTACATCCCAGAAACAC

CACCACCTGGATATATCAGTGAAGATGGAGAAACAAGTGACCAACAGT

TGAACCAAAGTATGGACACAGGCTCTCCGGCTGAACTGTCTCCTACTA

CTCTCTCTCCTGTTAATCACAGCTTGGATTTGCAGCCAGTTACTTACT

CGGAACCTGCATTCTGGTGTTCAATCGCATACTATGAACTAAACCAGA

GGGTTGGAGAGACCTTCCATGCGTCACAGCCCTCGCTCACTGTAGACG

TABLE 6-continued

GCTTCACAGACCCATCAAACTCGGAGAGGTTCTGCTTAGGCTTGCTCT

CCAACGTTAACCGAAATGCCACTGTAGAAATGACAAGAAGACATATAG

GAAGGGGAGTGCGCTTGTATTACATAGGTGGGGAAGTGTTTGCTGAGT

GCCTAAGTGATAGTGCAATCTTTGTGCAGAGCCCCAACTGTAACCAGA

GATACGGCTGGCACCCTGCAACAGTGTGTAAGATCCCACCAGGCTGTA

ACCTGAAGATCTTCAACAACCAAGAATTTGCTGCTCTTCTGGCTCAGT

CTGTCAACCAGGGTTTTGAAGCCGTTTATCAGCTAACCCGAATGTGCA

CCATAAGAATGAGTTTTGTGAAGGGCTGGGGAGCAGAATATCGGAGGC

AGACAGTAACAAGTACTCCTTGCTGGATTGAACTTCATCTGAATGGCC

CTCTGCAGTGGCTGGACAAAGTATTAACTCAGATGGGATCCCCTTCAG

TGCGATGCTCAAGCATGTCGTAAACCCATCAAAGACTCGCTGTAACAG

CTCCTCCGTCGTAGTATTCATGTATGATCCCGTGGACTGTTTGCTATC

CAAAAATTCCAGAGCAAAAACAGCACTTGAGGTCTCATCAGTTAAAGC

ACCTTGTGGAATCTGTTTCCTATATTTGAATATTAGATGGGAAAATTA

GTGTCTAGAAATGCCCTCCCCAGCGAAAAAGAAGACTTAAA

TABLE 7

(Sequence ID NO:4)
MSSILPFTPPVVKRLLGWKKSAGGSSGGAGGGEQNGQEEKWCEKAVKSL

VKKLKKTGRLDELEKAITTQNCNTKCVTIPSTCSEIWGLSTPNTIDQW

DTTGLYSFSEQTRSLDGRLWVSHRKGLPHVIYCRLWRWPDLHSHHELK

AIENCEYAFNLKKDEVCVNPYHYQRVETPVLPPVLVPRHTEILTELPP

LDDYTHSIPENTNFPAGIEPQSNYIPETPPPGYISEDGETSDQQLNQS

MDTGSPAELSPTTLSPVNHSLDLQPVTYSEPAFWCSIAYYELNQRVGE

TFHASQPSLTVDGFTDPSNSERFCLGLLSNVNRNATVEMTRRHIGRGV

RLYYIGGEVFAECLSDSAIFVQSPNCNQRYGWHPATVCKIPPGCNLKI

FNNQEFAALLAQSVNQGFEAVYQLTRMCTIRMSFVKGWGAEYRRQTVT

STPCWIELHLNGPLQWLDKVLTQMGSPSVRCSSMS

We claim:

1. An isolated nucleic acid comprising a nucleotide sequence encoding a mammalian MAD-related 2 (MADR2) protein.

2. An isolated nucleic acid in accordance with claim 1 wherein the nucleic acid encodes a normal MADR2 protein and wherein the nucleotide sequence is selected from the group consisting of
   (a) a nucleotide sequence encoding a protein comprising the human MADR2 amino acid sequence of Sequence ID No.:2; and
   (b) a nucleotide sequence encoding a protein comprising the mouse MADR2 amino acid sequence of Sequence ID No.:4.

3. An isolated nucleic acid in accordance with claim 1 wherein the nucleic acid encodes a mutant MADR2 protein, wherein the nucleotide sequence encodes at least one mutation which corresponds to a mutation of Sequence ID No.:2 selected from the group consisting of P445H, L440R, D450E and R133C and wherein the nucleotide sequence otherwise corresponds to a nucleotide sequence selected from the group consisting of
   (a) a nucleotide sequence encoding a protein comprising the human MADR2 amino acid sequence of Sequence ID No.2; and
   (b) a nucleotide sequence encoding a protein comprising the mouse MADR2 amino acid sequence of Sequence ID No.:4.

4. An isolated nucleic acid in accordance with claim 1 comprising Sequence ID No:1.

5. An isolated nucleic acid in accordance with claim 1 comprising Sequence ID No:3.

6. An isolated nucleic acid comprising a recombinant vector including a nucleotide sequence of claim 1.

7. An isolated host cell transformed with a recombinant vector of claim 6.

8. An isolated nucleic acid comprising a nucleotide sequence selected from the group consisting of Sequence ID No:1, Sequence ID No:3 and a sequence complementary to any of these sequences.

9. An isolated nucleic acid encoding a human MADR2 protein encoded by the polynucleotide contained in the plasmid ATCC Accession #97691.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
        (A) LENGTH: 1605 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
TTTTCCTAGC GTGGCTTGCT GCCTTTGGTN AAGAACATGT CGTCCATCTT GCCATTCACG      60
CCGCCAGTTG TGAAGAGACT GCTGGGATGG AAGAAGTCAG CTGGTGGGTC TGGAGGAGCA     120
GGCGGAGGAG AGCAGAATGG GCAGGAAGAA AAGTGGTGTG AGAAAGCAGT GAAAAGTCTG     180
GTGAAGAAGC TAAAGAAAAC AGGACGATTA GATGAGCTTG AGAAAGCCAT CACCACTCAA     240
AACTGTAATA CTAAATGTGT TACCATACCA AGCACTTGCT CTGAAATTTG GGGACTGAGT     300
ACACCAAATA CGATAGATCA GTGGGATACA ACAGGCCTTT ACAGCTTCTC TGAACAAACC     360
AGGTCTCTTG ATGGTCGTCT CCAGGTATCC CATCGAAAAG GATTGCCACA TGTTATATAT     420
TGCCGATTAT GGCGCTGGCC TGATCTTCAC AGTCATCATG AACTCAAGGC AATTGAAAAC     480
TGCGAATATG CTTTTAATCT TAAAAAGGAT GAAGTATGTG TAAACCCTTA CCACTATCAG     540
AGAGTTGAGA CACCAGTTTT GCCTCCAGTA TTAGTGCCCC GACACACCGA GATCCTAACA     600
GAACTTCCGC CTCTGGATGA CTATACTCAC TCCATTCCAG AAAACACTAA CTTCCCAGCA     660
GGAATTGAGC CACAGAGTAA TTATATTCCA GAAACGCCAC CTCCTGGATA TATCAGTGAA     720
GATGGAGAAA CAAGTGACCA ACAGTTGAAT CAAAGTATGG ACACAGGCTC TCCAGCAGAA     780
CTATCTCCTA CTACTCTTTC CCCTGTTAAT CATAGCTTGG ATTTACAGCC AGTTACTTAC     840
TCAGAACCTG CATTTTGGTG TTCGATAGCA TATTATGAAT TAAATCAGAG GGTTGGAGAA     900
ACCTTCCATG CATCACAGCC CTCACTCACT GTAGATGGCT TTACAGACCC ATCAAATTCA     960
GAGAGGTTCT GCTTAGGTTT ACTCTCCAAT GTTAACCGAA ATGCCACGGT AGAAATGACA    1020
AGAAGGCATA TAGGAAGAGG AGTGCGCTTA TACTACATAG GTGGGAAGT TTTTGCTGAG     1080
TGCCTAAGTG ATAGTGCAAT CTTTGTGCAG AGCCCCAATT GTAATCAGAG ATATGGCTGG    1140
CACCCTGCAA CAGTGTGTAA AATTCCACCA GGCTGTAATC TGAAGATCTT CAACAACCAG    1200
GAATTTGCTG CTCTTCTGGC TCAGTCTGTT AATCAGGGTT TGAAGCCGT CTATCAGCTA     1260
ACTAGAATGT GCACCATAAG AATGAGTTTT GTGAAAGGGT GGGGAGCAGA ATACCGAAGG    1320
CAGACGGTAA CAAGTACTCC TTGCTGGATT GAACTTCATC TGAATGGACC TCTACAGTGG    1380
TTGGACAAAG TATTAACTCA GATGGGATCC CCTTCAGTGC GTTGCTCAAG CATGTCATAA    1440
AGCTTCACCA ATCAAGTCCC ATGGAAAAGA CTTAATGTAA CAACTCTTCT GTTCATTAGC    1500
ATTGTGTTGT NGTCCCTATG GGACTGTTTA CTATTCCAAA AGTTTCAAGG AGAGAAAACA    1560
GCANTTGAGG TCTCCNTCAT TTAAAGNACC CTGTNGGATT TTTTT                    1605
```

(2) INFORMATION FOR SEQ ID NO:2:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ser Ser Ile Leu Pro Phe Thr Pro Pro Val Val Lys Arg Leu Leu
1               5                   10                  15

Gly Trp Lys Lys Ser Ala Gly Gly Ser Gly Gly Ala Gly Gly Gly Glu
            20                  25                  30

Gln Asn Gly Gln Glu Glu Lys Trp Cys Glu Lys Ala Val Lys Ser Leu
            35                  40                  45

Val Lys Lys Leu Lys Lys Thr Gly Arg Leu Asp Glu Leu Glu Lys Ala
50                  55                  60

Ile Thr Thr Gln Asn Cys Asn Thr Lys Cys Val Thr Ile Pro Ser Thr
65                  70                  75                  80

Cys Ser Glu Ile Trp Gly Leu Ser Thr Pro Asn Thr Ile Asp Gln Trp
                85                  90                  95

Asp Thr Thr Gly Leu Tyr Ser Phe Ser Glu Gln Thr Arg Ser Leu Asp
                100                 105                 110

Gly Arg Leu Gln Val Ser His Arg Lys Gly Leu Pro His Val Ile Tyr
        115                 120                 125

Cys Arg Leu Trp Arg Trp Pro Asp Leu His Ser His His Glu Leu Lys
        130                 135                 140

Ala Ile Glu Asn Cys Glu Tyr Ala Phe Asn Leu Lys Lys Asp Glu Val
145                 150                 155                 160

Cys Val Asn Pro Tyr His Tyr Gln Arg Val Glu Thr Pro Val Leu Pro
                165                 170                 175

Pro Val Leu Val Pro Arg His Thr Glu Ile Leu Thr Glu Leu Pro Pro
            180                 185                 190

Leu Asp Asp Tyr Thr His Ser Ile Pro Glu Asn Thr Asn Phe Pro Ala
            195                 200                 205

Gly Ile Glu Pro Gln Ser Asn Tyr Ile Pro Glu Thr Pro Pro Pro Gly
        210                 215                 220

Tyr Ile Ser Glu Asp Gly Glu Thr Ser Asp Gln Gln Leu Asn Gln Ser
225                 230                 235                 240

Met Asp Thr Gly Ser Pro Ala Glu Leu Ser Pro Thr Thr Leu Ser Pro
                245                 250                 255

Val Asn His Ser Leu Asp Leu Gln Pro Val Thr Tyr Ser Glu Pro Ala
            260                 265                 270

Phe Trp Cys Ser Ile Ala Tyr Tyr Glu Leu Asn Gln Arg Val Gly Glu
            275                 280                 285

Thr Phe His Ala Ser Gln Pro Ser Leu Thr Val Asp Gly Phe Thr Asp
        290                 295                 300

Pro Ser Asn Ser Glu Arg Phe Cys Leu Gly Leu Leu Ser Asn Val Asn
305                 310                 315                 320

Arg Asn Ala Thr Val Glu Met Thr Arg Arg His Ile Gly Arg Gly Val
                325                 330                 335

Arg Leu Tyr Tyr Ile Gly Gly Glu Val Phe Ala Glu Cys Leu Ser Asp
            340                 345                 350

Ser Ala Ile Phe Val Gln Ser Pro Asn Cys Asn Gln Arg Tyr Gly Trp
            355                 360                 365

His Pro Ala Thr Val Cys Lys Ile Pro Pro Gly Cys Asn Leu Lys Ile
        370                 375                 380

Phe Asn Asn Gln Glu Phe Ala Ala Leu Leu Ala Gln Ser Val Asn Gln
385                 390                 395                 400

Gly Phe Glu Ala Val Tyr Gln Leu Thr Arg Met Cys Thr Ile Arg Met
                405                 410                 415
```

```
Ser Phe Val Lys Gly Trp Gly Ala Glu Tyr Arg Arg Gln Thr Val Thr
            420                 425                 430

Ser Thr Pro Cys Trp Ile Glu Leu His Leu Asn Gly Pro Leu Gln Trp
            435                 440                 445

Leu Asp Lys Val Leu Thr Gln Met Gly Ser Pro Ser Val Arg Cys Ser
    450                 455                 460

Ser Met Ser
465

(2) INFORMATION FOR SEQ ID NO:3:

(i) SEQUENCE CHARACTERISTICS:
        (A) LENGTH: 1721 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:
```

| | | | | | |
|---|---|---|---|---|---|
| AGGAACAAAA | GGTCCGGGGC | CCGGCTCGGA | CCCGGGGACC | AGGCGCTGGG | TGCAGGGTAG | 60 |
| ATTTACCGGG | CTTTTTCTGA | GTGTGGATTG | TTACCTTTGG | TAAGAAAATG | TCGTCCATCT | 120 |
| TGCCATTCAC | TCCGCCAGTG | GTGAAGAGAC | TTCTGGGATG | GAAAAAATCA | GCCGGTGGGT | 180 |
| CTGGAGGAGC | AGGTGGTGGA | GAGCAGAATG | GACAGGAAGA | AAAGTGGTGT | GAAAAAGCAG | 240 |
| TGAAAAGTCT | GGTGAAAAAG | CTAAAGAAAA | CAGGACGGTT | AGATGAGCTT | GAGAAAGCCA | 300 |
| TCACCACTCA | GAATTGCAAT | ACTAAATGTG | TCACCATACC | AAGCACTTGC | TCTGAAATTT | 360 |
| GGGGACTGAG | TACAGCAAAT | ACGGTAGATC | AGTGGGACAT | AACAGGCCTT | TACAGCTTCT | 420 |
| CTGAACAAAC | CAGGTCTCTT | GATGGCCGTC | TTCAGGTTTC | ACACCGGAAA | GGGTTGCCAC | 480 |
| ATGTTATATA | TTGCCGGCTC | TGGCGCTGGC | CGGACCTTCA | CAGTCATCAT | GAGCTCAAGG | 540 |
| CAATCGAAAA | CTGCGAATAT | GCTTTTAATC | TGAAAAAAGA | TGAAGTGTGT | GTAAATCCGT | 600 |
| ACCACTACCA | GAGAGTTGAG | ACCCCAGTCT | TGCCTCCAGT | CTTAGTGCCT | CGGCCAACGG | 660 |
| AGATTCTAAC | AGAACTGCCG | CCCCTGGATG | ACTACACCCA | CTCCATTCCA | GAAAACACAA | 720 |
| ATTTCCCAGC | AGGAATTGAG | CCACAGAGTA | ATTACATCCC | AGAAACACCA | CCACCTGGAT | 780 |
| ATATCAGTGA | AGATGGAGAA | ACAAGTGACC | AACAGTTGAA | CCAAAGTATG | GACACAGGCT | 840 |
| CTCCGGCTGA | ACTGTCTCCT | ACTACTCTCT | CTCCTGTTAA | TCACAGCTTG | GATTTGCAGC | 900 |
| CAGTTACTTA | CTCGGAACCT | GCATTCTGGT | GTTCAATCGC | ATACTATGAA | CTAAACCAGA | 960 |
| GGGTTGGAGA | GACCTTCCAT | GCGTCACAGC | CCTCGCTCAC | TGTAGACGGC | TTCACAGACC | 1020 |
| CATCAAACTC | GGAGAGGTTC | TGCTTAGGCT | TGCTCTCCAA | CGTTAACCGA | AATGCCACTG | 1080 |
| TAGAAATGAC | AAGAAGACAT | ATAGGAAGGG | GAGTGCGCTT | GTATTACATA | GGTGGGGAAG | 1140 |
| TGTTTGCTGA | GTGCCTAAGT | GATAGTGCAA | TCTTTGTGCA | GAGCCCCAAC | TGTAACCAGA | 1200 |
| GATACGGCTG | GCACCCTGCA | ACAGTGTGTA | AGATCCCACC | AGGCTGTAAC | CTGAAGATCT | 1260 |
| TCAACAACCA | AGAATTTGCT | GCTCTTCTGG | CTCAGTCTGT | CAACCAGGGT | TTTGAAGCCG | 1320 |
| TTTATCAGCT | AACCCGAATG | TGCACCATAA | GAATGAGTTT | TGTGAAGGGC | TGGGGAGCAG | 1380 |
| AATATCGGAG | GCAGACAGTA | ACAAGTACTC | CTTGCTGGAT | TGAACTTCAT | CTGAATGGCC | 1440 |
| CTCTGCAGTG | GCTGGACAAA | GTATTAACTC | AGATGGGATC | CCCTTCAGTG | CGATGCTCAA | 1500 |
| GCATGTCGTA | AACCCATCAA | AGACTCGCTG | TAACAGCTCC | TCCGTCGTAG | TATTCATGTA | 1560 |
| TGATCCCGTG | GACTGTTTGC | TATCCAAAAA | TTCCAGAGCA | AAAACAGCAC | TTGAGGTCTC | 1620 |

```
ATCAGTTAAA GCACCTTGTG GAATCTGTTT CCTATATTTG AATATTAGAT GGGAAAATTA      1680

GTGTCTAGAA ATGCCCTCCC CAGCGAAAAA GAAGACTTAA A                          1721
```

(2) INFORMATION FOR SEQ ID NO:4:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ser Ser Ile Leu Pro Phe Thr Pro Pro Val Val Lys Arg Leu Leu
1               5                   10                  15

Gly Trp Lys Lys Ser Ala Gly Gly Ser Gly Gly Ala Gly Gly Gly Glu
            20                  25                  30

Gln Asn Gly Gln Glu Glu Lys Trp Cys Glu Lys Ala Val Lys Ser Leu
        35                  40                  45

Val Lys Lys Leu Lys Lys Thr Gly Arg Leu Asp Glu Leu Glu Lys Ala
50                  55                  60

Ile Thr Thr Gln Asn Cys Asn Thr Lys Cys Val Thr Ile Pro Ser Thr
65                  70                  75                  80

Cys Ser Glu Ile Trp Gly Leu Ser Thr Ala Asn Thr Val Asp Gln Trp
                85                  90                  95

Asp Ile Thr Gly Leu Tyr Ser Phe Ser Glu Gln Thr Arg Ser Leu Asp
            100                 105                 110

Gly Arg Leu Gln Val Ser His Arg Lys Gly Leu Pro His Val Ile Tyr
        115                 120                 125

Cys Arg Leu Trp Arg Trp Pro Asp Leu His Ser His His Glu Leu Lys
130                 135                 140

Ala Ile Glu Asn Cys Glu Tyr Ala Phe Asn Leu Lys Lys Asp Glu Val
145                 150                 155                 160

Cys Val Asn Pro Tyr His Tyr Gln Arg Val Glu Thr Pro Val Leu Pro
                165                 170                 175

Pro Val Leu Val Pro Arg Pro Thr Glu Ile Leu Thr Glu Leu Pro Pro
            180                 185                 190

Leu Asp Asp Tyr Thr His Ser Ile Pro Glu Asn Thr Asn Phe Pro Ala
        195                 200                 205

Gly Ile Glu Pro Gln Ser Asn Tyr Ile Pro Glu Thr Pro Pro Pro Gly
210                 215                 220

Tyr Ile Ser Glu Asp Gly Glu Thr Ser Asp Gln Gln Leu Asn Gln Ser
225                 230                 235                 240

Met Asp Thr Gly Ser Pro Ala Glu Leu Ser Pro Thr Thr Leu Ser Pro
                245                 250                 255

Val Asn His Ser Leu Asp Leu Gln Pro Val Thr Tyr Ser Glu Pro Ala
            260                 265                 270

Phe Trp Cys Ser Ile Ala Tyr Tyr Glu Leu Asn Gln Arg Val Gly Glu
        275                 280                 285

Thr Phe His Ala Ser Gln Pro Ser Leu Thr Val Asp Gly Phe Thr Asp
290                 295                 300

Pro Ser Asn Ser Glu Arg Phe Cys Leu Gly Leu Leu Ser Asn Val Asn
305                 310                 315                 320

Arg Asn Ala Thr Val Glu Met Thr Arg Arg His Ile Gly Arg Gly Val
                325                 330                 335
```

-continued

```
Arg Leu Tyr Tyr Ile Gly Gly Glu Val Phe Ala Glu Cys Leu Ser Asp
            340                 345                 350

Ser Ala Ile Phe Val Gln Ser Pro Asn Cys Asn Gln Arg Tyr Gly Trp
            355                 360                 365

His Pro Ala Thr Val Cys Lys Ile Pro Pro Gly Cys Asn Leu Lys Ile
            370                 375                 380

Phe Asn Asn Gln Glu Phe Ala Ala Leu Leu Ala Gln Ser Val Asn Gln
385                 390                 395                 400

Gly Phe Glu Ala Val Tyr Gln Leu Thr Arg Met Cys Thr Ile Arg Met
            405                 410                 415

Ser Phe Val Lys Gly Trp Gly Ala Glu Tyr Arg Arg Gln Thr Val Thr
            420                 425                 430

Ser Thr Pro Cys Trp Ile Glu Leu His Leu Asn Gly Pro Leu Gln Trp
            435                 440                 445

Leu Asp Lys Val Leu Thr Gln Met Gly Ser Pro Ser Val Arg Cys Ser
450                 455                 460

Ser Met Ser
465
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (v) FRAGMENT TYPE: linear (xi) SEQUENCE DESCRIPTION: SEQ ID NO:5:

AGATCAGTGG GATACAACAG G                                  21

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (v) FRAGMENT TYPE: linear (xi) SEQUENCE DESCRIPTION: SEQ ID NO:6:

GGCACTAATC TGGAGGCAA                                    19

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (v) FRAGMENT TYPE: linear (xi) SEQUENCE DESCRIPTION: SEQ ID NO:7:

AGCTTGGATT TACAGCCAGT        20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (v) FRAGMENT TYPE: linear (xi) SEQUENCE DESCRIPTION: SEQ ID NO:8:

TAAGCTCACT CCTCTTCCTA        20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (v) FRAGMENT TYPE: linear (xi) SEQUENCE DESCRIPTION: SEQ ID NO:9:

GGCTCAGTCT GTTAATCAGG        20

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (v) FRAGMENT TYPE: linear (xi) SEQUENCE DESCRIPTION: SEQ ID NO:10:

TTCCATGGGA CTTGATTGGT T        21

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (v) FRAGMENT TYPE: linear -continued (xi) SEQUENCE DESCRIPTION: SEQ ID NO:11:

TGTTAACCGA AATGCCACGG                                               20

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (v) FRAGMENT TYPE: linear (xi) SEQUENCE DESCRIPTION: SEQ ID NO:12:

TCTTATGGTG CACATTCTAG T                                             21

(2) INFORMATION FOR SEQ ID NO:13:

(i) SEQUENCE CHARACTERISTICS:
        (A) LENGTH: 465 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Met Asn Val Thr Ser Leu Phe Ser Phe Thr Ser Pro Ala Val Lys Arg
1               5                   10                  15

Leu Leu Gly Trp Lys Gln Gly Asp Glu Glu Lys Trp Ala Glu Lys
            20                  25                  30

Ala Val Asp Ala Leu Val Lys Lys Leu Lys Lys Lys Gly Ala Met
        35                  40                  45

Glu Glu Leu Glu Lys Ala Leu Ser Cys Pro Gly Gln Pro Ser Asn Cys
 50                  55                  60

Val Thr Ile Pro Arg Ser Leu Asp Gly Arg Leu Gln Val Ser His Arg
65                   70                  75                  80

Lys Gly Leu Pro His Val Ile Tyr Cys Arg Val Trp Arg Trp Pro Asp
                85                  90                  95

Leu Gln Ser His His Glu Leu Lys Pro Leu Glu Cys Cys Glu Phe Pro
            100                 105                 110

Phe Gly Ser Lys Gln Lys Glu Val Cys Ile Asn Pro Tyr His Tyr Lys
        115                 120                 125

Arg Val Glu Ser Pro Val Leu Pro Pro Val Leu Val Pro Arg His Ser
130                 135                 140

Glu Tyr Asn Pro Gln His Ser Leu Leu Ala Gln Phe Arg Asn Leu Gly
145                 150                 155                 160

Gln Asn Glu Pro His Met Pro Leu Asn Ala Thr Phe Pro Asp Ser Phe
                165                 170                 175

Gln Gln Pro Asn Ser His Pro Phe Pro His Ser Pro Asn Ser Ser Tyr
            180                 185                 190

Pro Asn Ser Pro Gly Ser Ser Ser Ser Thr Tyr Pro His Ser Pro Thr
        195                 200                 205

Ser Ser Asp Pro Gly Ser Pro Phe Gln Met Pro Ala Asp Thr Pro Pro
210                 215                 220

Pro Ala Tyr Leu Pro Pro Glu Asp Pro Met Thr Gln Asp Gly Ser Gln
225                 230                 235                 240
```

```
Pro Met Asp Thr Asn Met Met Ala Pro Pro Leu Pro Ser Glu Ile Asn
            245                 250                 255

Arg Gly Asp Val Gln Ala Val Ala Tyr Glu Glu Pro Lys His Trp Cys
        260                 265                 270

Ser Ile Val Tyr Tyr Glu Leu Asn Asn Arg Val Gly Glu Ala Phe His
            275                 280                 285

Ala Ser Ser Thr Ser Val Leu Val Asp Gly Phe Thr Asp Pro Ser Asn
        290                 295                 300

Asn Lys Asn Arg Phe Cys Leu Gly Leu Leu Ser Asn Val Asn Arg Asn
305                 310                 315                 320

Ser Thr Ile Glu Asn Thr Arg Arg His Ile Gly Lys Gly Val His Leu
            325                 330                 335

Tyr Tyr Val Gly Gly Glu Val Tyr Ala Glu Cys Leu Ser Asp Ser Ser
            340                 345                 350

Ile Phe Val Gln Ser Arg Asn Cys Asn Tyr His His Gly Phe His Pro
            355                 360                 365

Thr Thr Val Cys Lys Ile Pro Ser Gly Cys Ser Leu Lys Ile Phe Asn
            370                 375                 380

Asn Gln Glu Phe Ala Gln Leu Leu Ala Gln Ser Val Asn His Gly Phe
385                 390                 395                 400

Glu Thr Val Tyr Glu Leu Thr Lys Met Cys Thr Ile Arg Met Ser Phe
            405                 410                 415

Val Lys Gly Trp Gly Ala Glu Tyr His Arg Gln Asp Val Thr Ser Thr
            420                 425                 430

Pro Cys Trp Ile Glu Ile His Leu His Gly Pro Leu Gln Trp Leu Asp
            435                 440                 445

Lys Val Leu Thr Gln Met Gly Ser Pro His Asn Pro Ile Ser Ser Val
450                 455                 460

Ser

465

(2) INFORMATION FOR SEQ ID NO:14:

(i) SEQUENCE CHARACTERISTICS:
        (A) LENGTH: 552 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Met Asp Asn Met Ser Ile Thr Asn Thr Pro Thr Ser Asn Asp Ala Cys
1               5                   10                  15

Leu Ser Ile Val His Ser Leu Met Cys His Arg Gln Gly Gly Glu Ser
            20                  25                  30

Glu Thr Phe Ala Lys Arg Ala Ile Glu Ser Leu Val Lys Lys Leu Lys
            35                  40                  45

Glu Lys Lys Asp Glu Leu Asp Ser Leu Ile Thr Ala Ile Thr Thr Asn
        50                  55                  60

Gly Ala His Pro Ser Lys Cys Val Thr Ile Gln Arg Thr Leu Asp Gly
65              70                  75                  80

Arg Leu Gln Val Ala Gly Arg Lys Gly Phe Pro His Val Ile Tyr Ala
            85                  90                  95

Arg Leu Trp Arg Trp Pro Asp Leu His Lys Asn Glu Leu Lys His Val
            100                 105                 110
```

-continued

```
Lys Tyr Cys Gln Tyr Ala Phe Asp Leu Lys Cys Asp Ser Val Cys Val
    115                 120                 125
Asn Pro Tyr His Tyr Glu Arg Val Val Ser Pro Gly Ile Asp Leu Ser
130                 135                 140
Gly Leu Thr Leu Gln Ser Asn Ala Pro Ser Ser Met Met Val Lys Asp
145                 150                 155                 160
Glu Tyr Val His Asp Phe Glu Gly Gln Pro Ser Leu Ser Thr Glu Gly
                165                 170                 175
His Ser Ile Gln Thr Ile Gln His Pro Pro Ser Asn Arg Ala Ser Thr
            180                 185                 190
Glu Thr Tyr Ser Thr Pro Ala Leu Leu Ala Pro Ser Glu Ser Asn Ala
        195                 200                 205
Thr Ser Thr Ala Asn Phe Pro Asn Ile Pro Val Ala Ser Thr Ser Gln
    210                 215                 220
Pro Ala Ser Ile Leu Gly Gly Ser His Ser Glu Gly Leu Leu Gln Ile
225                 230                 235                 240
Ala Ser Gly Pro Gln Pro Gly Gln Gln Asn Gly Phe Thr Gly Gln
                245                 250                 255
Pro Ala Thr Tyr His His Asn Ser Thr Thr Trp Thr Gly Ser Arg
                260                 265                 270
Thr Ala Pro Tyr Thr Pro Asn Leu Pro His His Gln Asn Gly His Leu
        275                 280                 285
Gln His His Pro Pro Met Pro Pro His Pro Gly His Tyr Trp Pro Val
    290                 295                 300
His Asn Glu Leu Ala Phe Gln Pro Pro Ile Ser Asn His Pro Ala Pro
305                 310                 315                 320
Glu Tyr Trp Cys Ser Ile Ala Tyr Phe Glu Met Asp Val Gln Val Gly
                325                 330                 335
Glu Thr Phe Lys Val Pro Ser Ser Cys Pro Ile Val Thr Val Asp Gly
            340                 345                 350
Tyr Val Asp Pro Ser Gly Gly Asp Arg Phe Cys Leu Gly Gln Leu Ser
        355                 360                 365
Asn Val His Arg Thr Glu Ala Ile Glu Arg Ala Arg Leu His Ile Gly
    370                 375                 380
Lys Gly Val Gln Leu Glu Cys Lys Gly Glu Gly Asp Val Trp Val Arg
385                 390                 395                 400
Cys Leu Ser Asp His Ala Val Phe Val Gln Ser Tyr Tyr Leu Asp Arg
                405                 410                 415
Glu Ala Gly Arg Ala Pro Gly Asp Ala Val His Lys Ile Tyr Pro Ser
            420                 425                 430
Ala Tyr Ile Lys Val Phe Asp Leu Arg Gln Cys His Arg Gln Met Gln
        435                 440                 445
Gln Gln Ala Ala Thr Ala Gln Ala Ala Ala Ala Gln Ala Ala Ala
    450                 455                 460
Val Ala Gly Asn Ile Pro Gly Pro Gly Ser Val Gly Gly Ile Ala Pro
465                 470                 475                 480
Ala Ile Ser Leu Ser Ala Ala Ala Gly Ile Gly Val Asp Asp Leu Arg
                485                 490                 495
Arg Leu Cys Ile Leu Arg Met Ser Phe Val Lys Gly Trp Gly Pro Asp
            500                 505                 510
Tyr Pro Arg Gln Ser Ile Lys Glu Thr Pro Cys Trp Ile Glu Ile His
        515                 520                 525
Leu His Arg Ala Leu Gln Leu Leu Asp Glu Val Leu His Thr Met Pro
    530                 535                 540
```

```
Ile Ala Asp Pro Gln Pro Leu Asp
545                 550

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (v) FRAGMENT TYPE: linear (xi) SEQUENCE DESCRIPTION: SEQ ID NO:15:

Arg Leu Trp Arg Trp Pro Asp Leu
1               5

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (v) FRAGMENT TYPE: linear (xi) SEQUENCE DESCRIPTION: SEQ ID NO:16:

Glu Ile His Leu His Arg Ala Leu Gln Leu Leu Asp Glu Val Leu
1               5                   10                  15

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (v) FRAGMENT TYPE: linear (xi) SEQUENCE DESCRIPTION: SEQ ID NO:17:

Arg Val Trp Arg Trp Pro Asp Leu
1               5

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (v) FRAGMENT TYPE: linear (xi) SEQUENCE DESCRIPTION: SEQ ID NO:18:

Glu Ile His Leu His Gly Pro Leu Gln Trp Leu Asp Lys Val Leu
1               5                   10                  15

(2) INFORMATION FOR SEQ ID NO:19:

(i) SEQUENCE CHARACTERISTICS:
```

(A) LENGTH: 8 amino acids
        (B) TYPE: amino acid
        (C) STRANDEDNESS: single
        (D) TOPOLOGY: linear (ii) MOLECULE TYPE: peptide (v) FRAGMENT TYPE: linear (xi) SEQUENCE DESCRIPTION: SEQ ID NO:19:

Arg Leu Trp Arg Trp Pro Asp Leu
1               5

(2) INFORMATION FOR SEQ ID NO:20:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (v) FRAGMENT TYPE: linear (xi) SEQUENCE DESCRIPTION: SEQ ID NO:20:

Glu Leu His Leu Asn Gly Pro Leu Gln Trp Leu Asp Lys Val Leu
1               5                   10                  15

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (v) FRAGMENT TYPE: linear (xi) SEQUENCE DESCRIPTION: SEQ ID NO:21:

ACCAATCAAG TCCCATGAAA                                                    20

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (v) FRAGMENT TYPE: linear (xi) SEQUENCE DESCRIPTION: SEQ ID NO:22:

TGATCGAGAC CTCAAGTGCT G                                                  21

(2) INFORMATION FOR SEQ ID NO:23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (v) FRAGMENT TYPE: linear

```
    (xi) SEQUENCE DESCRIPTION: SEQ ID NO:23:

ATTGAAATTC ACTTACACCG GG                                                        22

(2) INFORMATION FOR SEQ ID NO:24:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (v) FRAGMENT TYPE: linear (xi) SEQUENCE DESCRIPTION: SEQ ID NO:24:

AGCCATGCCT GACAAGTTCT                                                           20
```